United States Patent
Schlingensiepen et al.

(10) Patent No.: US 8,822,425 B2
(45) Date of Patent: Sep. 2, 2014

(54) DOSAGE OF OLIGONUCLEOTIDES SUITABLE FOR THE TREATMENT OF TUMORS

(75) Inventors: Karl-Hermann Schlingensiepen, Donaustauf (DE); Hubert Heinrichs, Regensburg (DE); Susanne Schmaus, Grossberg-Pentling (DE)

(73) Assignee: Antisense Pharma GmbH, Regensburg (DE)

( * ) Notice: Subject to any disclaimer, the term of this patent is extended or adjusted under 35 U.S.C. 154(b) by 43 days.

(21) Appl. No.: 12/453,487

(22) Filed: May 12, 2009

(65) Prior Publication Data

US 2010/0286236 A1 Nov. 11, 2010

(51) Int. Cl.
C12N 15/11 (2006.01)
C07H 21/04 (2006.01)

(52) U.S. Cl.
USPC ........................................ 514/44 A; 536/24.5

(58) Field of Classification Search
None
See application file for complete search history.

(56) References Cited

U.S. PATENT DOCUMENTS

| | | | | |
|---|---|---|---|---|
| 6,455,689 | B1 * | 9/2002 | Schlingensiepen et al. . | 536/24.5 |
| 7,273,932 | B1 * | 9/2007 | LaBarbera et al. ........... | 536/24.5 |
| 2003/0105035 | A1 * | 6/2003 | Agrawal ........................ | 514/44 |

FOREIGN PATENT DOCUMENTS

| EP | 1008649 A | 6/2000 |
|---|---|---|
| WO | WO 99/63975 A | 12/1999 |
| WO | WO 2004/104197 A | 12/2004 |
| WO | WO 2005/059133 | 6/2005 |
| WO | WO 2005/084712 * | 9/2005 |
| WO | WO 2006/117400 A | 11/2006 |

OTHER PUBLICATIONS

Oettle et al (Journal of Clinical Oncology, 2006 ASCO Annual Meeting Proceedings Part I. vol. 24, No. 18S (Jun. 20 Supplement), 2006:14012).*
Von Hoff et al (N. Engl. J. Med. 369: 1691-1703, 2013).*
Yoo et al (Br. J. Cancer 101: 1658-1663, 2009).*
Hauschild et al (J. Clin. Oncol. 27(17): 2823-2830, 2009).*
Daylon et al (Annals of Oncology 00:1-6, 2013).*
Hodi et al (N Engl. J. Med. Aug. 19, 2010;363(8):711-23).*
Pelzer et al (European Journal of Cancer 4 7 ( 2 0 1 1 ) 1 6 7 6-1 6 8 1).*
Schlingensiepen Weimar et al: "Intra cerebral and intrathecal infusion of the TGF-beta 2-specific antisense phosphorothioate oligonucleotide AP 12009 in rabbits an" OLIGO primates: Toxicology and safety:Nucleotides, vol. 15, No. 2, 2005, pp. 94-104, XP002523633 ISSN: 1545-4576.
Schlingensiepen K H et al: "Targeted tumor therapy with the TGF-beta2 antisense compound AP 12009" Cytosine and Growth Factor Reviews, vol. 17, No. 1-2, Feb. 1, 2006, pp. 129-139, XP024987943.
Jansen B et al.: "Antisense therapy for cander-the time of truth" Lancet Oncology, vol. 3, No. 11, Nov. 1, 2002, pp. 672-683, XP004810743 ISSN: 1470-2045.
Tamm et al.: "Antisense therapy in oncology: new hope for an old idea?" Lancet the, vol. 358, No. 9280, Aug. 11, 2001, pp. 489-497, XP005018285; ISSN: 0140-6736.
Karl-Herman Schlingensiepen et al., "Antisense Therapeutics for Tumor Treatment: The TGF-beta2 Inhibitor AP 12009 in Clinical Development Against Malignant Tumors," Recent Results in Cancer Research, vol. 177, 2008, pp. 137-150.
Retrieved from the Internet: http://ncifrederick.cancer.gov/Lasp/Acuc/Frederick/Media/Documents/ACUC42.pdf.
Emil J. Freireich et al., "Quantitative Comparison of Toxicity of Anticancer Agents in Mouse, Rat, Hamster, Dog, Monkey and Man," Cancer Chemotherapy Reports, vol. 50, May 1966, pp. 219-244.

* cited by examiner

*Primary Examiner* — Richard Schnizer
(74) *Attorney, Agent, or Firm* — Jacobson Holman, PLLC.

(57) ABSTRACT

A method for preventing and/or treating a tumor, the method comprising: intravenously administering an antisense oligonucleotide in an amount of between about 400 to about 800 mg/m$^2$/treatment cycle, the antisense oligonucleotide comprises 8 to 30 nucleotide building blocks, which hybridizes with mRNA of TGF-beta-2, -1 and/or -3 for the preparation of a pharmaceutical composition.

8 Claims, 8 Drawing Sheets

| Target | SEQ ID NO | Sequences |
|---|---|---|
| TGF-beta 1 | 1 | ctgatgtgttgaagaaca |
| | 2 | cgatagtcttgcag |
| | 3 | gtcgatagtcttgc |
| | 4 | cttggacaggatct |
| | 5 | ccaggaattgttgc |
| | 6 | cctcaatttcccct |
| | 7 | gatgtccacttgca |
| | 8 | ctccaaatgtaggg |
| | 9 | accttgctgtactg |
| | 10 | gtagtacacgatgg |
| | 11 | cacgtagtacacga |
| | 12 | catgttggacagct |
| | 13 | gcacgatcatgttg |
| | 14 | tgtactctgcttgaac |
| | 15 | ctctgatgtgttgaag |
| | 16 | ggaagtcaatgtacag |
| | 17 | catgtcgatagtcttgca |
| | 18 | agctgaagcaatagttgg |
| | 19 | gtcatagatttcgttgtg |
| | 20 | ctccacttttaacttgag |
| | 21 | tgctgtatttctggtaca |
| TGF-beta 2 | 22 | cggcatgtctattttgta |
| | 23 | gctttcaccaaattggaagc |
| | 24 | ctggcttttgggtt |
| | 25 | cacacagtagtgca |
| | 26 | gcacacagtagtgc |
| | 27 | gcttgctcaggatctgc |
| | 28 | tactcttcgtcgct |
| | 29 | cttggcgtagtact |
| | 30 | gtaaacctccttgg |
| | 31 | gtctattttgtaaacctcc |
| | 32 | gcatgtctattttgtaaacc |
| | 33 | ggcatcaaggtacc |
| | 34 | ctgtagaaagtggg |
| | 35 | acaattctgaagtagggt |
| | 36 | tcaccaaattggaagcat |
| | 37 | tctgatatagctcaatcc |
| | 38 | tcctagtggactttatag |
| | 39 | tttttcctagtggact |
| | 40 | caattatcctgcacatttc |
| | 41 | gcaattatcctgcaca |
| | 42 | gcagcaattatcctgc |
| | 43 | tggcattgtaccct |
| | 44 | tgtgctgagtgtct |
| | 45 | cctgctgtgctgagtg |
| TGF-beta 3 | 46 | cttgggtgttttgc |
| | 47 | tttagctgcatttgcaag |
| | 48 | gccacttttccaag |
| | 49 | tcgagcttccccca |
| | 50 | ccccgagcccaagg |
| | 51 | cccgacgagccgg |
| | 52 | acgcaccaaggcga |
| | 53 | cgggttgtcgagccc |
| | 54 | cggcagtgccccg |
| | 55 | cgcaattctgctcg |
| | 56 | ttcgttgtgctccc |
| | 57 | attccgactcggtg |
| | 58 | acgtgcgtcatcaccgt |
| | 59 | ccaagaagcc |
| | 60 | cctaatgccttcca |
| | 61 | tcagcagggccagg |
| | 62 | gcaaagttcagcagggc |
| | 63 | ggcaaagttcagcagg |
| | 64 | gtggcaaagttcagcagg |
| | 65 | gtggcaaagttcag |
| | 66 | gaccgtggcaaagttcag |
| | 67 | agagaggctgaccgt |
| | 68 | gagagagagaggctgac |
| | 69 | acagagagaggctga |
| | 70 | gtggacagagagagg |
| | 71 | caactggacagagagagg |
| | 72 | tcttcttgatgtggcc |
| | 73 | ccctcttcttcttgatg |
| | 74 | caccctcttcttct |
| | 75 | atggatttctttggcat |
| | 76 | ggatttctttggc |
| | 77 | aagttggactctcttctc |
| | 78 | taagttggactctcttct |
| Prostaglandin E$_2$ | 79 | taggagtggttgaggc |
| | 80 | gtgtaggagtggttgag |
| | 81 | ctgtgtaggagtgg |
| | 82 | cccacatgcctgtg |
| | 83 | cgatgaacaacgag |
| | 84 | ctggcgatgaacaacg |
| | 85 | cgctggcgatgaac |
| | 86 | gagctagtcccgttg |
| | 87 | gcgaagagctagtcc |
| | 88 | ccagttatgcgaagagc |
| | 89 | ccccagttatgcgaag |
| VEGF | 90 | cggccgcggtgt |
| | 91 | cgggaatgcttccgccg |
| | 92 | cggctcaccgcctcggc |
| | 93 | cacgtctgcggatc |

FIG. 1A

|  |  |  |  |
|---|---|---|---|
| | 94 ccccgcatcgcatcaggg | | 143 tcagctatcccagagc |
| | 95 cgccttgcaacgcg | | 144 ggctgggtcagctat |
| | 96 ccgaccggggccgg | | 145 aaatcgttcacagagaag |
| | 97 gttcatggtttcgg | | 146 tctttctaaatcgttcac |
| | 98 gcagaaagttcatgg | c-jun | 147 tcggactatactgc |
| | 99 gctgatagacatcc | | 148 cagttcggactatact |
| | 100 gcgctgatagacat | | 149 aagcctaagacgca |
| | 101 gtagctgcgctgatag | | 150 gcccaagttcaaca |
| | 102 ctcgatctcatcag | | 151 tgaaaagtcgcggt |
| | 103 atgtactcgatctcatc | | 152 ggttaattaagatgcctc |
| | 104 gaagatgtactcgatc | | 153 tctctaagagcgca |
| | 105 cttgaagatgtactcg | | 154 acgtgaggttagtttg |
| | 106 gcatcgcatcaggg | | 155 cacgtgaggttagt |
| | 107 ccgcatcgcatcag | | 156 catagaacagtccg |
| | 108 catttgttgtgctgtagg | | 157 cagtcatagaacagtc |
| | 109 ggtctgcattcacatttg | | 158 ctttgcagtcatagaaca |
| | 110 ctttggtctgcattc | | 159 tgcagtcatagaaac |
| | 111 ctttctttggtctgc | | 160 ggtcgtttccatct |
| | 112 gctctatctttctttgg | | 161 catagaaggtcgtttc |
| | 113 gtcttgctctatctttc | | 162 cgtcatagaaggtc |
| | 114 cttgtcttgctctatc | | 163 catcgtcatagaagg |
| | 115 catctgcaagtacgttcg | | 164 ggacgggaggaacgaggcgttgag |
| | 116 cacatctgcaagtacgtt | | 165 tagccataaggtcc |
| | 117 gtcacatctgcaagtacg | | 166 ggttactgtagcca |
| | 118 catctgcaagtacg | | 167 ggttactgtagcca |
| | 119 cacatctgcaagtac | | 168 cagggtcatg ctctgtttca ggatcttggg |
| | 120 gtcacatctgcaag | | 169 agttcttggcgcggaggt |
| | 121 cttgtcacatctgc | | 170 aggtgaggaggtccgagt |
| | 122 ggcttgtcacatctgc | | 171 tggactggattatcag |
| | 123 ctcggcttgtcacatc | | 172 gtggtggtgatgtgcccg |
| | 124 ctccttcctcctgc | | 173 tgtcacgttcttgg |
| | 125 gcttgaagatgtacctcg | | 174 ctcatctgtcacgt |
| | 126 cgttgctctccgacg | | 175 cgaagccctcggcgaacc |
| IL-10 | 127 cttcttttgcaagtctgt | | 176 gcgtgttctggctgtgcagttcgg |
| | 128 tgagctgtgcatgccttc | | 177 ctgccccgttgacc |
| | 129 agtcaggaggaccag | | 178 aggtttgcgtagac |
| | 130 tgggtgccctggcct | | 179 ggttgaagttgctg |
| | 131 catgttaggcaggtt | | 180 ctgggttgaagttg |
| | 132 aggcatctcggagatct | | 181 tgctggggtt gcgcgggaaa ggcc |
| | 133 aaagtcttcactctgc | | 182 tgctgcacgggcatctgctg |
| | 134 aacaagttgtccagctg | | 183 ggcactgtctgaggctcctccttcagg |
| | 135 gtaaaactggatcatctc | | 184 actccatgtcgatg |
| | 136 catcacctcctccag | | 185 ctctccgccttgatcc |
| | 137 gggtcttcaggttctccc | | 186 gttcctcatgcgcttc |
| | 138 cacggccttgctcttgtt | | 187 ctgagctttcaagg |
| | 139 ttattaaaggcattcttc | | 188 gcgattctctccagcttccttttcg |
| | 140 aagatgtcaaactcactc | | 189 ctgagctttcaaggttttcacttttcctc |
| | 141 gtagttgatgaagatgtc | | 190 tccctgagcatgtt |
| | 142 gattttggagacctct | | 191 tctgtttaagctgtgc |

FIG. 1B c-fos

| | |
|---|---|
| 192 | ctttctgtttaagctgtg |
| 193 | ggttcatgactttctg |
| 194 | cgtggttcatgact |
| 195 | actgttaacgtggttc |
| 196 | ccactgttaacgtg |
| 197 | cccactgttaacgt |
| 198 | agcatgagttggca |
| 199 | gcgttagcatgagt |
| 200 | gtttgcaactgctg |
| 201 | caaaatgtttgcaactgc |
| 202 | tcgtagaaggtcgt |
| 203 | agggttactgtagc |
| 204 | gtagtggtgatgtg |
| 205 | cgtcgtagaaggtc |
| 206 | cgagaacatcatcg |
| 207 | gtagtctgcgttga |
| 208 | gctgcagcgggaggatgacg |
| 209 | agtaagagaggctatc |
| 210 | gtagtaagagaggc |
| 211 | ggtagtaagagagg |
| 212 | gtgagtggtagtaaga |
| 213 | gtccgtgcagaagtcctg |
| 214 | gaatgaagttggcact |
| 215 | ggaatgaagttggc |
| 216 | gggaatgaagttgg |
| 217 | gctgcaccagccactgcaggtccggactgg |
| 218 | ctggtctgcg atggggccac agaggagacg |
| 219 | tcatggtcttcacaac |
| 220 | caatgctctgcgctcggcctcctgtcatgg |
| 221 | ctagagttcctcac |
| 222 | gagtacgctagagt |
| 223 | gaagagtacgctag |
| 224 | ctgcttcccacccagcccccacattccc |
| 225 | ttcatcctctgtactgggct |
| 226 | gttacggatgtgca |
| 227 | cagttacggatgtg |
| 228 | ccagttacggatgt |
| 229 | agagtctgagttgg |
| 230 | gtgagactcagagt |
| 231 | tcttagggtgagac |
| 232 | gagagtacttcttagg |
| 233 | ggaagaaactatgagagt |
| 234 | cttagggaagaaactatg |
| 235 | cggtaagaaacttagg |
| 236 | agcatgcggtaaga |
| 237 | gtctgaaagcatgc |
| 238 | agaacaaagaagagcc |
| 239 | caagagaacaaagaagag |
| 240 | cagcaagagaacaaag |

| | |
|---|---|
| 241 | tcctcagcaagaga |
| 242 | aggtgtgacttgca |
| 243 | gaataggtgtgacttg |
| 244 | cagaataggtgtgact |
| 245 | gcagaataggtgtg |
| 246 | cagttgcagaataggt |
| 247 | gaaaccatttctgacc |
| 248 | tgtgaaaccatttctgac |
| 249 | cactgtgaaaccatttct |
| 250 | ccactgtgaaacca |
| 251 | agaactggctcctgcagcttccctgcttcc |
| 252 | cacctccattcaccc |
| 253 | cagtaaaagtgtctgc |
| 254 | cgacattcagtaaaagtg |
| 255 | gaccgacattcagt |
| 256 | cttctggagataactaga |
| 257 | catcttattcctttccct |
| 258 | cagccatcttattcct |
| 259 | tgcagccatcttattc |
| 260 | gagtgtatcagtcag |
| 261 | ggagtgtatcagtc |
| 262 | cttggagtgtatcagt |
| 263 | acagagtacctacc |
| 264 | ccaactttcccttaag |
| 265 | ccttatgctcaatctc |
| 266 | gtcttactcaaggg |
| 267 | acagtcttactcaagg |
| 268 | cataagacacagtcttac |
| 269 | gaaagcataagacacagt |
| 270 | ggaaagcataagacac |
| 271 | agggataaaggaaagc |
| 272 | cctgtatacagagg |
| 273 | tgtctcctgtatacag |
| 274 | catcttctagttggtc |
| 275 | ctcatcttctagttgg |
| 276 | cttctcatcttctagttg |
| 277 | caaagcagacttctca |
| 278 | ctgcaaagcagact |
| 279 | ctagttttttccttctcct |
| 280 | tctagtttttccttctcc |
| 281 | caggatgaactctagt |
| 282 | cgagaacatcatgg |
| 283 | gtagtaggaaaggc |
| 284 | ggtagtaggaaagg |
| 285 | ggaatggtagtagg |
| 286 | ggtcattgagaagag |
| 287 | gctaatgttcttgacc |
| 288 | gtcaggaatcggcag |
| 289 | cttggagaagacatac |

MIA

FIG. 1C

| | |
|---|---|
| 290 | tgcctccccagaag |
| 291 | cactggcagtagaaatc |
| 292 | gctcactggcagtag |
| 293 | atggtcaggaatcg |
| 294 | gaatggtcaggaatcg |
| 295 | catcgtggactgtg |
| 296 | agccatggagatag |
| 297 | cagccatggagatag |
| 298 | acagccatggagatag |
| 299 | cacagccatggagatag |
| 300 | ccacagccatggagat |
| 301 | gccatggagatagg |
| 302 | agccatggagatagg |
| 303 | cagccatggagatagg |
| 304 | acagccatggagatagg |
| 305 | catggagatagggt |
| 306 | catggagatagggtg |
| 307 | catggagatagggtgg |
| 308 | atggagatagggtg |
| 309 | atggagatagggtgg |
| 310 | atggagatagggtggc |
| 311 | atggagatagggtggct |
| 312 | ggagatagggtggc |
| 313 | ggagatagggtggct |
| 314 | gaaatagcccaggc |
| 315 | gaaatagcccaggcg |
| 316 | gaaatagcccaggcgag |
| 317 | ggaaatagcccagg |
| 318 | ggaaatagcccaggc |
| 319 | gtcttcacatcgac |
| 320 | gtcttcacatcgact |
| 321 | gtcttcacatcgactt |
| 322 | gtcttcacatcgacttt |
| 323 | gtcttcacatcgactttg |
| 324 | gtcttcacatcgactttg |
| 325 | ccatttgtctgtcttcac |

FIG. 1D

1st Schedule: 7 days on / 7 days off

2nd Schedule: 4 days on / 10 days off

SEQUENCE LISTING

```
<160> NUMBER OF SEQ ID NOS: 325

<210> SEQ ID NO 1
<211> LENGTH: 18
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 1
ctgatgtgtt gaagaaca                                                 18

<210> SEQ ID NO 2
<211> LENGTH: 14
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 2
cgatagtctt gcag                                                     14

<210> SEQ ID NO 3
<211> LENGTH: 14
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 3
gtcgatagtc ttgc                                                     14

<210> SEQ ID NO 4
<211> LENGTH: 14
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 4
cttggacagg atct                                                     14

<210> SEQ ID NO 5
<211> LENGTH: 14
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 5
ccaggaattg ttgc                                                     14

<210> SEQ ID NO 6
<211> LENGTH: 14
<212> TYPE: DNA
<213> ORGANISM: Artificial Sequence
```

```
<220> FEATURE:
<223> OTHER INFORMATION: oligonucleotides hybridizing with TGF-beta 1

<400> SEQUENCE: 6
cctcaatttc ccct                                                     14

<210> SEQ ID NO 7
<211> LENGTH: 14
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 7
gatgtccact tgca                                                     14

<210> SEQ ID NO 8
<211> LENGTH: 14
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 8
ctccaaatgt aggg                                                     14

<210> SEQ ID NO 9
<211> LENGTH: 14
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 9
accttgctgt actg                                                     14

<210> SEQ ID NO 10
<211> LENGTH: 14
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 10
gtagtacacg atgg                                                     14

<210> SEQ ID NO 11
<211> LENGTH: 14
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 11
cacgtagtac acga                                                     14

<210> SEQ ID NO 12
<211> LENGTH: 14
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 12
catgttggac agct                                                     14
```

```
<210> SEQ ID NO 13
<211> LENGTH: 14
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 13
gcacgatcat gttg                                                     14

<210> SEQ ID NO 14
<211> LENGTH: 16
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 14
tgtactctgc ttgaac                                                   16

<210> SEQ ID NO 15
<211> LENGTH: 16
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 15
ctctgatgtg ttgaag                                                   16

<210> SEQ ID NO 16
<211> LENGTH: 16
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 16
ggaagtcaat gtacag                                                   16

<210> SEQ ID NO 17
<211> LENGTH: 18
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 17
catgtcgata gtcttgca                                                 18

<210> SEQ ID NO 18
<211> LENGTH: 18
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 18
agctgaagca atagttgg                                                 18

<210> SEQ ID NO 19
<211> LENGTH: 18
<212> TYPE: DNA
<213> ORGANISM: Artificial Sequence
<220> FEATURE:
<223> OTHER INFORMATION: oligonucleotides hybridizing with TGF-beta 1
```

```
<400> SEQUENCE: 19
gtcatagatt tcgttgtg                                            18

<210> SEQ ID NO 20
<211> LENGTH: 18
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 20
ctccactttt aacttgag                                            18

<210> SEQ ID NO 21
<211> LENGTH: 18
<212> TYPE: DNA
<213> ORGANISM: Artificial Sequence
<220> FEATURE:
<223> OTHER INFORMATION: oligonucleotides hybridizing with TGF-beta 1

<400> SEQUENCE: 21
tgctgtattt ctggtaca                                            18

<210> SEQ ID NO 22
<211> LENGTH: 18
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 22
cggcatgtct attttgta                                            18

<210> SEQ ID NO 23
<211> LENGTH: 20
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 23
gctttcacca aattggaagc                                          20

<210> SEQ ID NO 24
<211> LENGTH: 14
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 24
ctggcttttg ggtt                                                14

<210> SEQ ID NO 25
<211> LENGTH: 14
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 25
cacacagtag tgca                                                14

<210> SEQ ID NO 26
```

```
<211> LENGTH: 14
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 26
gcacacagta gtgc                                                        14

<210> SEQ ID NO 27
<211> LENGTH: 17
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 27
gcttgctcag gatctgc                                                     17

<210> SEQ ID NO 28
<211> LENGTH: 14
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 28
tactcttcgt cgct                                                        14

<210> SEQ ID NO 29
<211> LENGTH: 14
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 29
cttggcgtag tact                                                        14

<210> SEQ ID NO 30
<211> LENGTH: 14
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 30
gtaaacctcc ttgg                                                        14

<210> SEQ ID NO 31
<211> LENGTH: 19
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 31
gtctattttg taaacctcc                                                   19

<210> SEQ ID NO 32
<211> LENGTH: 20
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 32
```

```
gcatgtctat tttgtaaacc                                          20

<210> SEQ ID NO 33
<211> LENGTH: 14
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 33
ggcatcaagg tacc                                                14

<210> SEQ ID NO 34
<211> LENGTH: 14
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 34
ctgtagaaag tggg                                                14

<210> SEQ ID NO 35
<211> LENGTH: 18
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 35
acaattctga agtagggt                                            18

<210> SEQ ID NO 36
<211> LENGTH: 18
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 36
tcaccaaatt ggaagcat                                            18

<210> SEQ ID NO 37
<211> LENGTH: 18
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 37
tctgatatag ctcaatcc                                            18

<210> SEQ ID NO 38
<211> LENGTH: 18
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 38
tcctagtgga ctttatag                                            18

<210> SEQ ID NO 39
<211> LENGTH: 16
<212> TYPE: DNA
```

```
<213> ORGANISM: Artificial Sequence
<220> FEATURE:
<223> OTHER INFORMATION: oligonucleotides hybridizing with TGF-beta 2

<400> SEQUENCE: 39
tttttcctag tggact                                                    16

<210> SEQ ID NO 40
<211> LENGTH: 19
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 40
caattatcct gcacatttc                                                 19

<210> SEQ ID NO 41
<211> LENGTH: 16
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 41
gcaattatcc tgcaca                                                    16

<210> SEQ ID NO 42
<211> LENGTH: 16
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 42
gcagcaatta tcctgc                                                    16

<210> SEQ ID NO 43
<211> LENGTH: 14
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 43
tggcattgta ccct                                                      14

<210> SEQ ID NO 44
<211> LENGTH: 14
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 44
tgtgctgagt gtct                                                      14

<210> SEQ ID NO 45
<211> LENGTH: 16
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 45
cctgctgtgc tgagtg                                                    16
```

<210> SEQ ID NO 46
<211> LENGTH: 14
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 46
cttgggtgtt ttgc                                                    14

<210> SEQ ID NO 47
<211> LENGTH: 18
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 47
tttagctgca tttgcaag                                                18

<210> SEQ ID NO 48
<211> LENGTH: 14
<212> TYPE: DNA
<213> ORGANISM: Artificial Sequence
<220> FEATURE:
<223> OTHER INFORMATION: oligonucleotides hybridizing with TGF-beta 2

<400> SEQUENCE: 48 gccactttc caag                                                     14

<210> SEQ ID NO 49
<211> LENGTH: 14
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 49
tcgagcttcc ccca                                                    14

<210> SEQ ID NO 50
<211> LENGTH: 14
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 50
ccccgagccc aagg                                                    14

<210> SEQ ID NO 51
<211> LENGTH: 13
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 51
cccgacgagc cgg                                                     13

<210> SEQ ID NO 52
<211> LENGTH: 14
<212> TYPE: DNA
<213> ORGANISM: Artificial Sequence
<220> FEATURE:

```
<223> OTHER INFORMATION: oligonucleotides hybridizing with TGF-beta 3

<400> SEQUENCE: 52
acgcaccaag gcga                                                         14

<210> SEQ ID NO 53
<211> LENGTH: 15
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 53
cgggttgtcg agccc                                                        15

<210> SEQ ID NO 54
<211> LENGTH: 13
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 54
cggcagtgcc ccg                                                          13

<210> SEQ ID NO 55
<211> LENGTH: 14
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 55
cgcaattctg ctcg                                                         14

<210> SEQ ID NO 56
<211> LENGTH: 14
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 56
ttcgttgtgc tccc                                                         14

<210> SEQ ID NO 57
<211> LENGTH: 14
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 57
attccgactc ggtg                                                         14

<210> SEQ ID NO 58
<211> LENGTH: 17
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 58
acgtgcgtca tcaccgt                                                      17
```

```
<210> SEQ ID NO 59
<211> LENGTH: 10
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 59
ccaagaagcc                                                          10

<210> SEQ ID NO 60
<211> LENGTH: 14
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 60
cctaatgcct tcca                                                     14

<210> SEQ ID NO 61
<211> LENGTH: 14
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 61
tcagcagggc cagg                                                     14

<210> SEQ ID NO 62
<211> LENGTH: 17
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 62
gcaaagttca gcagggc                                                  17

<210> SEQ ID NO 63
<211> LENGTH: 16
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 63
ggcaaagttc agcagg                                                   16

<210> SEQ ID NO 64
<211> LENGTH: 18
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 64
gtggcaaagt tcagcagg                                                 18

<210> SEQ ID NO 65
<211> LENGTH: 14
<212> TYPE: DNA
<213> ORGANISM: Artificial Sequence
<220> FEATURE:
<223> OTHER INFORMATION: oligonucleotides hybridizing with TGF-beta 3
```

<400> SEQUENCE: 65
gtggcaaagt tcag                                                         14

<210> SEQ ID NO 66
<211> LENGTH: 18
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 66
gaccgtggca aagttcag                                                     18

<210> SEQ ID NO 67
<211> LENGTH: 15
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 67
agagaggctg accgt                                                        15

<210> SEQ ID NO 68
<211> LENGTH: 17
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 68
gagagagaga ggctgac                                                      17

<210> SEQ ID NO 69
<211> LENGTH: 15
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 69
acagagagag gctga                                                        15

<210> SEQ ID NO 70
<211> LENGTH: 15
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 70
gtggacagag agagg                                                        15

<210> SEQ ID NO 71
<211> LENGTH: 18
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 71
caactggaca gagagagg                                                     18

<210> SEQ ID NO 72
<211> LENGTH: 16

```
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 72
tcttcttgat gtggcc                                                    16

<210> SEQ ID NO 73
<211> LENGTH: 17
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 73
ccctcttctt cttgatg                                                   17

<210> SEQ ID NO 74
<211> LENGTH: 14
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 74
caccctcttc ttct                                                      14

<210> SEQ ID NO 75
<211> LENGTH: 17
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 75
atggatttct ttggcat                                                   17

<210> SEQ ID NO 76
<211> LENGTH: 13
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 76
ggatttcttt ggc                                                       13

<210> SEQ ID NO 77
<211> LENGTH: 18
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 77
aagttggact ctcttctc                                                  18

<210> SEQ ID NO 78
<211> LENGTH: 18
<212> TYPE: DNA
<213> ORGANISM: Artificial Sequence
<220> FEATURE:
<223> OTHER INFORMATION: oligonucleotides hybridizing with TGF-beta 3

<400> SEQUENCE: 78
```

```
taagttggac tctcttct                                                 18

<210> SEQ ID NO 79
<211> LENGTH: 16
<212> TYPE: DNA
<213> ORGANISM: Artificial Sequence
<220> FEATURE:
<223> OTHER INFORMATION: oligonucleotides hybridizing with Prostagladin
      E2

<400> SEQUENCE: 79
taggagtggt tgaggc                                                   16

<210> SEQ ID NO 80
<211> LENGTH: 17
<212> TYPE: DNA
<213> ORGANISM: Artificial Sequence
<220> FEATURE:
<223> OTHER INFORMATION: oligonucleotides hybridizing with Prostagladin
      E2

<400> SEQUENCE: 80
gtgtaggagt ggttgag                                                  17

<210> SEQ ID NO 81
<211> LENGTH: 14
<212> TYPE: DNA
<213> ORGANISM: Artificial Sequence
<220> FEATURE:
<223> OTHER INFORMATION: oligonucleotides hybridizing with Prostagladin
      E2

<400> SEQUENCE: 81
ctgtgtagga gtgg                                                     14

<210> SEQ ID NO 82
<211> LENGTH: 14
<212> TYPE: DNA
<213> ORGANISM: Artificial Sequence
<220> FEATURE:
<223> OTHER INFORMATION: oligonucleotides hybridizing with Prostagladin
      E2

<400> SEQUENCE: 82
cccacatgcc tgtg                                                     14

<210> SEQ ID NO 83
<211> LENGTH: 14
<212> TYPE: DNA
<213> ORGANISM: Artificial Sequence
<220> FEATURE:
<223> OTHER INFORMATION: oligonucleotides hybridizing with Prostagladin
      E2

<400> SEQUENCE: 83
cgatgaacaa cgag                                                     14

<210> SEQ ID NO 84
<211> LENGTH: 16
<212> TYPE: DNA
<213> ORGANISM: Artificial Sequence
<220> FEATURE:
<223> OTHER INFORMATION: oligonucleotides hybridizing with Prostagladin
      E2

<400> SEQUENCE: 84
ctggcgatga acaacg                                                   16
```

```
<210> SEQ ID NO 85
<211> LENGTH: 14
<212> TYPE: DNA
<213> ORGANISM: Artificial Sequence
<220> FEATURE:
<223> OTHER INFORMATION: oligonucleotides hybridizing with Prostagladin
      E2

<400> SEQUENCE: 85
cgctggcgat gaac                                                       14

<210> SEQ ID NO 86
<211> LENGTH: 15
<212> TYPE: DNA
<213> ORGANISM: Artificial Sequence
<220> FEATURE:
<223> OTHER INFORMATION: oligonucleotides hybridizing with Prostagladin
      E2

<400> SEQUENCE: 86
gagctagtcc cgttg                                                      15

<210> SEQ ID NO 87
<211> LENGTH: 15
<212> TYPE: DNA
<213> ORGANISM: Artificial Sequence
<220> FEATURE:
<223> OTHER INFORMATION: oligonucleotides hybridizing with Prostagladin
      E2

<400> SEQUENCE: 87
gcgaagagct agtcc                                                      15

<210> SEQ ID NO 88
<211> LENGTH: 17
<212> TYPE: DNA
<213> ORGANISM: Artificial Sequence
<220> FEATURE:
<223> OTHER INFORMATION: oligonucleotides hybridizing with Prostagladin
      E2

<400> SEQUENCE: 88
ccagttatgc gaagagc                                                    17

<210> SEQ ID NO 89
<211> LENGTH: 16
<212> TYPE: DNA
<213> ORGANISM: Artificial Sequence
<220> FEATURE:
<223> OTHER INFORMATION: oligonucleotides hybridizing with Prostagladin
      E2

<400> SEQUENCE: 89
ccccagttat gcgaag                                                     16

<210> SEQ ID NO 90
<211> LENGTH: 14
<212> TYPE: DNA
<213> ORGANISM: Artificial Sequence
<220> FEATURE:
<223> OTHER INFORMATION: oligonucleotides hybridizing with VEGF

<400> SEQUENCE: 90
cggccgcggt gtgt                                                       14
```

```
<210> SEQ ID NO 91
<211> LENGTH: 17
<212> TYPE: DNA
<213> ORGANISM: Artificial Sequence
<220> FEATURE:
<223> OTHER INFORMATION: oligonucleotides hybridizing with VEGF

<400> SEQUENCE: 91
cgggaatgct tccgccg                                                  17

<210> SEQ ID NO 92
<211> LENGTH: 17
<212> TYPE: DNA
<213> ORGANISM: Artificial Sequence
<220> FEATURE:
<223> OTHER INFORMATION: oligonucleotides hybridizing with VEGF

<400> SEQUENCE: 92
cggctcaccg cctcggc                                                  17

<210> SEQ ID NO 93
<211> LENGTH: 14
<212> TYPE: DNA
<213> ORGANISM: Artificial Sequence
<220> FEATURE:
<223> OTHER INFORMATION: oligonucleotides hybridizing with VEGF

<400> SEQUENCE: 93
cacgtctgcg gatc                                                     14

<210> SEQ ID NO 94
<211> LENGTH: 18
<212> TYPE: DNA
<213> ORGANISM: Artificial Sequence
<220> FEATURE:
<223> OTHER INFORMATION: oligonucleotides hybridizing with VEGF

<400> SEQUENCE: 94
ccccgcatcg catcaggg                                                 18

<210> SEQ ID NO 95
<211> LENGTH: 14
<212> TYPE: DNA
<213> ORGANISM: Artificial Sequence
<220> FEATURE:
<223> OTHER INFORMATION: oligonucleotides hybridizing with VEGF

<400> SEQUENCE: 95
cgccttgcaa cgcg                                                     14

<210> SEQ ID NO 96
<211> LENGTH: 14
<212> TYPE: DNA
<213> ORGANISM: Artificial Sequence
<220> FEATURE:
<223> OTHER INFORMATION: oligonucleotides hybridizing with VEGF

<400> SEQUENCE: 96
ccgaccgggg ccgg                                                     14

<210> SEQ ID NO 97
<211> LENGTH: 14
<212> TYPE: DNA
<213> ORGANISM: Artificial Sequence
<220> FEATURE:
<223> OTHER INFORMATION: oligonucleotides hybridizing with VEGF
```

```
<400> SEQUENCE: 97
gttcatggtt tcgg                                                     14

<210> SEQ ID NO 98
<211> LENGTH: 15
<212> TYPE: DNA
<213> ORGANISM: Artificial Sequence
<220> FEATURE:
<223> OTHER INFORMATION: oligonucleotides hybridizing with VEGF

<400> SEQUENCE: 98
gcagaaagtt catgg                                                    15

<210> SEQ ID NO 99
<211> LENGTH: 14
<212> TYPE: DNA
<213> ORGANISM: Artificial Sequence
<220> FEATURE:
<223> OTHER INFORMATION: oligonucleotides hybridizing with VEGF

<400> SEQUENCE: 99
gctgatagac atcc                                                     14

<210> SEQ ID NO 100
<211> LENGTH: 14
<212> TYPE: DNA
<213> ORGANISM: Artificial Sequence
<220> FEATURE:
<223> OTHER INFORMATION: oligonucleotides hybridizing with VEGF

<400> SEQUENCE: 100
gcgctgatag acat                                                     14

<210> SEQ ID NO 101
<211> LENGTH: 16
<212> TYPE: DNA
<213> ORGANISM: Artificial Sequence
<220> FEATURE:
<223> OTHER INFORMATION: oligonucleotides hybridizing with VEGF

<400> SEQUENCE: 101
gtagctgcgc tgatag                                                   16

<210> SEQ ID NO 102
<211> LENGTH: 14
<212> TYPE: DNA
<213> ORGANISM: Artificial Sequence
<220> FEATURE:
<223> OTHER INFORMATION: oligonucleotides hybridizing with VEGF

<400> SEQUENCE: 102
ctcgatctca tcag                                                     14

<210> SEQ ID NO 103
<211> LENGTH: 17
<212> TYPE: DNA
<213> ORGANISM: Artificial Sequence
<220> FEATURE:
<223> OTHER INFORMATION: oligonucleotides hybridizing with VEGF

<400> SEQUENCE: 103
atgtactcga tctcatc                                                  17

<210> SEQ ID NO 104
<211> LENGTH: 16
```

<212> TYPE: DNA
<213> ORGANISM: Artificial Sequence
<220> FEATURE:
<223> OTHER INFORMATION: oligonucleotides hybridizing with VEGF

<400> SEQUENCE: 104
gaagatgtac tcgatc                                               16

<210> SEQ ID NO 105
<211> LENGTH: 16
<212> TYPE: DNA
<213> ORGANISM: Artificial Sequence
<220> FEATURE:
<223> OTHER INFORMATION: oligonucleotides hybridizing with VEGF

<400> SEQUENCE: 105
cttgaagatg tactcg                                               16

<210> SEQ ID NO 106
<211> LENGTH: 14
<212> TYPE: DNA
<213> ORGANISM: Artificial Sequence
<220> FEATURE:
<223> OTHER INFORMATION: oligonucleotides hybridizing with VEGF

<400> SEQUENCE: 106
gcatcgcatc aggg                                                 14

<210> SEQ ID NO 107
<211> LENGTH: 14
<212> TYPE: DNA
<213> ORGANISM: Artificial Sequence
<220> FEATURE:
<223> OTHER INFORMATION: oligonucleotides hybridizing with VEGF

<400> SEQUENCE: 107
ccgcatcgca tcag                                                 14

<210> SEQ ID NO 108
<211> LENGTH: 18
<212> TYPE: DNA
<213> ORGANISM: Artificial Sequence
<220> FEATURE:
<223> OTHER INFORMATION: oligonucleotides hybridizing with VEGF

<400> SEQUENCE: 108
catttgttgt gctgtagg                                             18

<210> SEQ ID NO 109
<211> LENGTH: 18
<212> TYPE: DNA
<213> ORGANISM: Artificial Sequence
<220> FEATURE:
<223> OTHER INFORMATION: oligonucleotides hybridizing with VEGF

<400> SEQUENCE: 109
ggtctgcatt cacatttg                                             18

<210> SEQ ID NO 110
<211> LENGTH: 15
<212> TYPE: DNA
<213> ORGANISM: Artificial Sequence
<220> FEATURE:
<223> OTHER INFORMATION: oligonucleotides hybridizing with VEGF

<400> SEQUENCE: 110
ctttggtctg cattc                                              15

<210> SEQ ID NO 111
<211> LENGTH: 15
<212> TYPE: DNA
<213> ORGANISM: Artificial Sequence
<220> FEATURE:
<223> OTHER INFORMATION: oligonucleotides hybridizing with VEGF

<400> SEQUENCE: 111
ctttctttgg tctgc                                              15

<210> SEQ ID NO 112
<211> LENGTH: 17
<212> TYPE: DNA
<213> ORGANISM: Artificial Sequence
<220> FEATURE:
<223> OTHER INFORMATION: oligonucleotides hybridizing with VEGF

<400> SEQUENCE: 112
gctctatctt tctttgg                                            17

<210> SEQ ID NO 113
<211> LENGTH: 17
<212> TYPE: DNA
<213> ORGANISM: Artificial Sequence
<220> FEATURE:
<223> OTHER INFORMATION: oligonucleotides hybridizing with VEGF

<400> SEQUENCE: 113
gtcttgctct atctttc                                            17

<210> SEQ ID NO 114
<211> LENGTH: 16
<212> TYPE: DNA
<213> ORGANISM: Artificial Sequence
<220> FEATURE:
<223> OTHER INFORMATION: oligonucleotides hybridizing with VEGF

<400> SEQUENCE: 114
cttgtcttgc tctatc                                             16

<210> SEQ ID NO 115
<211> LENGTH: 18
<212> TYPE: DNA
<213> ORGANISM: Artificial Sequence
<220> FEATURE:
<223> OTHER INFORMATION: oligonucleotides hybridizing with VEGF

<400> SEQUENCE: 115
catctgcaag tacgttcg                                           18

<210> SEQ ID NO 116
<211> LENGTH: 18
<212> TYPE: DNA
<213> ORGANISM: Artificial Sequence
<220> FEATURE:
<223> OTHER INFORMATION: oligonucleotides hybridizing with VEGF

<400> SEQUENCE: 116
cacatctgca agtacgtt                                           18

<210> SEQ ID NO 117
<211> LENGTH: 18
<212> TYPE: DNA
<213> ORGANISM: Artificial Sequence

```
<220> FEATURE:
<223> OTHER INFORMATION: oligonucleotides hybridizing with VEGF

<400> SEQUENCE: 117
gtcacatctg caagtacg                                                18

<210> SEQ ID NO 118
<211> LENGTH: 14
<212> TYPE: DNA
<213> ORGANISM: Artificial Sequence
<220> FEATURE:
<223> OTHER INFORMATION: oligonucleotides hybridizing with VEGF

<400> SEQUENCE: 118
catctgcaag tacg                                                    14

<210> SEQ ID NO 119
<211> LENGTH: 15
<212> TYPE: DNA
<213> ORGANISM: Artificial Sequence
<220> FEATURE:
<223> OTHER INFORMATION: oligonucleotides hybridizing with VEGF

<400> SEQUENCE: 119
cacatctgca agtac                                                   15

<210> SEQ ID NO 120
<211> LENGTH: 14
<212> TYPE: DNA
<213> ORGANISM: Artificial Sequence
<220> FEATURE:
<223> OTHER INFORMATION: oligonucleotides hybridizing with VEGF

<400> SEQUENCE: 120
gtcacatctg caag                                                    14

<210> SEQ ID NO 121
<211> LENGTH: 14
<212> TYPE: DNA
<213> ORGANISM: Artificial Sequence
<220> FEATURE:
<223> OTHER INFORMATION: oligonucleotides hybridizing with VEGF

<400> SEQUENCE: 121
cttgtcacat ctgc                                                    14

<210> SEQ ID NO 122
<211> LENGTH: 16
<212> TYPE: DNA
<213> ORGANISM: Artificial Sequence
<220> FEATURE:
<223> OTHER INFORMATION: oligonucleotides hybridizing with VEGF

<400> SEQUENCE: 122
ggcttgtcac atctgc                                                  16

<210> SEQ ID NO 123
<211> LENGTH: 16
<212> TYPE: DNA
<213> ORGANISM: Artificial Sequence
<220> FEATURE:
<223> OTHER INFORMATION: oligonucleotides hybridizing with VEGF

<400> SEQUENCE: 123
ctcggcttgt cacatc                                                  16
```

```
<210> SEQ ID NO 124
<211> LENGTH: 14
<212> TYPE: DNA
<213> ORGANISM: Artificial Sequence
<220> FEATURE:
<223> OTHER INFORMATION: oligonucleotides hybridizing with VEGF

<400> SEQUENCE: 124
ctccttcctc ctgc                                                    14

<210> SEQ ID NO 125
<211> LENGTH: 18
<212> TYPE: DNA
<213> ORGANISM: Artificial Sequence
<220> FEATURE:
<223> OTHER INFORMATION: oligonucleotides hybridizing with VEGF

<400> SEQUENCE: 125
gcttgaagat gtacctcg                                                18

<210> SEQ ID NO 126
<211> LENGTH: 15
<212> TYPE: DNA
<213> ORGANISM: Artificial Sequence
<220> FEATURE:
<223> OTHER INFORMATION: oligonucleotides hybridizing with VEGF

<400> SEQUENCE: 126
cgttgctctc cgacg                                                   15

<210> SEQ ID NO 127
<211> LENGTH: 18
<212> TYPE: DNA
<213> ORGANISM: Artificial Sequence
<220> FEATURE:
<223> OTHER INFORMATION: oligonucleotides hybridizing with IL-10

<400> SEQUENCE: 127
cttcttttgc aagtctgt                                                18

<210> SEQ ID NO 128
<211> LENGTH: 18
<212> TYPE: DNA
<213> ORGANISM: Artificial Sequence
<220> FEATURE:
<223> OTHER INFORMATION: oligonucleotides hybridizing with IL-10

<400> SEQUENCE: 128
tgagctgtgc atgccttc                                                18

<210> SEQ ID NO 129
<211> LENGTH: 15
<212> TYPE: DNA
<213> ORGANISM: Artificial Sequence
<220> FEATURE:
<223> OTHER INFORMATION: oligonucleotides hybridizing with IL-10

<400> SEQUENCE: 129
agtcaggagg accag                                                   15

<210> SEQ ID NO 130
<211> LENGTH: 15
<212> TYPE: DNA
<213> ORGANISM: Artificial Sequence
<220> FEATURE:
<223> OTHER INFORMATION: oligonucleotides hybridizing with IL-10
```

```
<400> SEQUENCE: 130
tgggtgccct ggcct                                                    15

<210> SEQ ID NO 131
<211> LENGTH: 15
<212> TYPE: DNA
<213> ORGANISM: Artificial Sequence
<220> FEATURE:
<223> OTHER INFORMATION: oligonucleotides hybridizing with IL-10

<400> SEQUENCE: 131
catgttaggc aggtt                                                    15

<210> SEQ ID NO 132
<211> LENGTH: 17
<212> TYPE: DNA
<213> ORGANISM: Artificial Sequence
<220> FEATURE:
<223> OTHER INFORMATION: oligonucleotides hybridizing with IL-10

<400> SEQUENCE: 132
aggcatctcg gagatct                                                  17

<210> SEQ ID NO 133
<211> LENGTH: 16
<212> TYPE: DNA
<213> ORGANISM: Artificial Sequence
<220> FEATURE:
<223> OTHER INFORMATION: oligonucleotides hybridizing with IL-10

<400> SEQUENCE: 133
aaagtcttca ctctgc                                                   16

<210> SEQ ID NO 134
<211> LENGTH: 17
<212> TYPE: DNA
<213> ORGANISM: Artificial Sequence
<220> FEATURE:
<223> OTHER INFORMATION: oligonucleotides hybridizing with IL-10

<400> SEQUENCE: 134
aacaagttgt ccagctg                                                  17

<210> SEQ ID NO 135
<211> LENGTH: 18
<212> TYPE: DNA
<213> ORGANISM: Artificial Sequence
<220> FEATURE:
<223> OTHER INFORMATION: oligonucleotides hybridizing with IL-10

<400> SEQUENCE: 135
gtaaaactgg atcatctc                                                 18

<210> SEQ ID NO 136
<211> LENGTH: 15
<212> TYPE: DNA
<213> ORGANISM: Artificial Sequence
<220> FEATURE:
<223> OTHER INFORMATION: oligonucleotides hybridizing with IL-10

<400> SEQUENCE: 136
catcacctcc tccag                                                    15

<210> SEQ ID NO 137
```

```
<211> LENGTH: 18
<212> TYPE: DNA
<213> ORGANISM: Artificial Sequence
<220> FEATURE:
<223> OTHER INFORMATION: oligonucleotides hybridizing with IL-10

<400> SEQUENCE: 137
gggtcttcag gttctccc                                                  18

<210> SEQ ID NO 138
<211> LENGTH: 18
<212> TYPE: DNA
<213> ORGANISM: Artificial Sequence
<220> FEATURE:
<223> OTHER INFORMATION: oligonucleotides hybridizing with IL-10

<400> SEQUENCE: 138
cacggccttg ctcttgtt                                                  18

<210> SEQ ID NO 139
<211> LENGTH: 18
<212> TYPE: DNA
<213> ORGANISM: Artificial Sequence
<220> FEATURE:
<223> OTHER INFORMATION: oligonucleotides hybridizing with IL-10

<400> SEQUENCE: 139
ttattaaagg cattcttc                                                  18

<210> SEQ ID NO 140
<211> LENGTH: 18
<212> TYPE: DNA
<213> ORGANISM: Artificial Sequence
<220> FEATURE:
<223> OTHER INFORMATION: oligonucleotides hybridizing with IL-10

<400> SEQUENCE: 140
aagatgtcaa actcactc                                                  18

<210> SEQ ID NO 141
<211> LENGTH: 18
<212> TYPE: DNA
<213> ORGANISM: Artificial Sequence
<220> FEATURE:
<223> OTHER INFORMATION: oligonucleotides hybridizing with IL-10

<400> SEQUENCE: 141
gtagttgatg aagatgtc                                                  18

<210> SEQ ID NO 142
<211> LENGTH: 16
<212> TYPE: DNA
<213> ORGANISM: Artificial Sequence
<220> FEATURE:
<223> OTHER INFORMATION: oligonucleotides hybridizing with IL-10

<400> SEQUENCE: 142
gattttggag acctct                                                    16

<210> SEQ ID NO 143
<211> LENGTH: 16
<212> TYPE: DNA
<213> ORGANISM: Artificial Sequence
<220> FEATURE:
<223> OTHER INFORMATION: oligonucleotides hybridizing with IL-10

<400> SEQUENCE: 143
```
tcagctatcc cagagc                                                    16

<210> SEQ ID NO 144
<211> LENGTH: 15
<212> TYPE: DNA
<213> ORGANISM: Artificial Sequence
<220> FEATURE:
<223> OTHER INFORMATION: oligonucleotides hybridizing with IL-10

<400> SEQUENCE: 144
ggctgggtca gctat                                                     15

<210> SEQ ID NO 145
<211> LENGTH: 18
<212> TYPE: DNA
<213> ORGANISM: Artificial Sequence
<220> FEATURE:
<223> OTHER INFORMATION: oligonucleotides hybridizing with IL-10

<400> SEQUENCE: 145
aaatcgttca cagagaag                                                  18

<210> SEQ ID NO 146
<211> LENGTH: 18
<212> TYPE: DNA
<213> ORGANISM: Artificial Sequence
<220> FEATURE:
<223> OTHER INFORMATION: oligonucleotides hybridizing with IL-10

<400> SEQUENCE: 146
tctttctaaa tcgttcac                                                  18

<210> SEQ ID NO 147
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 147
tcggactata ctgc                                                      14

<210> SEQ ID NO 148
<211> LENGTH: 16
<212> TYPE: DNA
<213> ORGANISM: Artificial Sequence
<220> FEATURE:
<223> OTHER INFORMATION: oligonucleotides hybridizing with c-jun

<400> SEQUENCE: 148
cagttcggac tatact                                                    16

<210> SEQ ID NO 149
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 149
aagcctaaga cgca                                                      14

<210> SEQ ID NO 150
<211> LENGTH: 14
<212> TYPE: DNA

```
<213> ORGANISM: Artificial Sequence
<220> FEATURE:
<223> OTHER INFORMATION: oligonucleotides hybridizing with c-jun

<400> SEQUENCE: 150
gcccaagttc aaca                                                    14

<210> SEQ ID NO 151
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 151
tgaaaagtcg cggt                                                    14

<210> SEQ ID NO 152
<211> LENGTH: 18
<212> TYPE: DNA
<213> ORGANISM: Artificial Sequence
<220> FEATURE:
<223> OTHER INFORMATION: oligonucleotides hybridizing with c-jun

<400> SEQUENCE: 152
ggttaattaa gatgcctc                                                18

<210> SEQ ID NO 153
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 153
tctctaagag cgca                                                    14

<210> SEQ ID NO 154
<211> LENGTH: 16
<212> TYPE: DNA
<213> ORGANISM: Artificial Sequence
<220> FEATURE:
<223> OTHER INFORMATION: oligonucleotides hybridizing with c-jun

<400> SEQUENCE: 154
acgtgaggtt agtttg                                                  16

<210> SEQ ID NO 155
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 155
cacgtgaggt tagt                                                    14

<210> SEQ ID NO 156
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 156
catagaacag tccg                                                    14
```

<210> SEQ ID NO 157
<211> LENGTH: 16
<212> TYPE: DNA
<213> ORGANISM: Artificial Sequence
<220> FEATURE:
<223> OTHER INFORMATION: oligonucleotides hybridizing with c-jun

<400> SEQUENCE: 157
cagtcataga acagtc                                                16

<210> SEQ ID NO 158
<211> LENGTH: 18
<212> TYPE: DNA
<213> ORGANISM: Artificial Sequence
<220> FEATURE:
<223> OTHER INFORMATION: oligonucleotides hybridizing with c-jun

<400> SEQUENCE: 158
ctttgcagtc atagaaca                                              18

<210> SEQ ID NO 159
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 159
tgcagtcata gaac                                                  14

<210> SEQ ID NO 160
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 160
ggtcgtttcc atct                                                  14

<210> SEQ ID NO 161
<211> LENGTH: 16
<212> TYPE: DNA
<213> ORGANISM: Artificial Sequence
<220> FEATURE:
<223> OTHER INFORMATION: oligonucleotides hybridizing with c-jun

<400> SEQUENCE: 161
catagaaggt cgtttc                                                16

<210> SEQ ID NO 162
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 162
cgtcatagaa ggtc                                                  14

<210> SEQ ID NO 163
<211> LENGTH: 15
<212> TYPE: DNA
<213> ORGANISM: Artificial Sequence
<220> FEATURE:

<223> OTHER INFORMATION: oligonucleotides hybridizing with c-jun

<400> SEQUENCE: 163
catcgtcata gaagg                                                    15

<210> SEQ ID NO 164
<211> LENGTH: 24
<212> TYPE: DNA
<213> ORGANISM: Artificial Sequence
<220> FEATURE:
<223> OTHER INFORMATION: oligonucleotides hybridizing with c-jun

<400> SEQUENCE: 164
ggacgggagg aacgaggcgt tgag                                          24

<210> SEQ ID NO 165
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 165
tagccataag gtcc                                                     14

<210> SEQ ID NO 166
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 166
ggttactgta gcca                                                     14

<210> SEQ ID NO 167
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 167
ggttactgta gcca                                                     14

<210> SEQ ID NO 168
<211> LENGTH: 30
<212> TYPE: DNA
<213> ORGANISM: Artificial Sequence
<220> FEATURE:
<223> OTHER INFORMATION: oligonucleotides hybridizing with c-jun

<400> SEQUENCE: 168
cagggtcatg ctctgtttca ggatcttggg                                    30

<210> SEQ ID NO 169
<211> LENGTH: 18
<212> TYPE: DNA
<213> ORGANISM: Artificial Sequence
<220> FEATURE:
<223> OTHER INFORMATION: oligonucleotides hybridizing with c-jun

<400> SEQUENCE: 169
agttcttggc gcggaggt                                                 18

```
<210> SEQ ID NO 170
<211> LENGTH: 18
<212> TYPE: DNA
<213> ORGANISM: Artificial Sequence
<220> FEATURE:
<223> OTHER INFORMATION: oligonucleotides hybridizing with c-jun

<400> SEQUENCE: 170
aggtgaggag gtccgagt                                                    18

<210> SEQ ID NO 171
<211> LENGTH: 16
<212> TYPE: DNA
<213> ORGANISM: Artificial Sequence
<220> FEATURE:
<223> OTHER INFORMATION: oligonucleotides hybridizing with c-jun

<400> SEQUENCE: 171
tggactggat tatcag                                                      16

<210> SEQ ID NO 172
<211> LENGTH: 18
<212> TYPE: DNA
<213> ORGANISM: Artificial Sequence
<220> FEATURE:
<223> OTHER INFORMATION: oligonucleotides hybridizing with c-jun

<400> SEQUENCE: 172
gtggtggtga tgtgcccg                                                    18

<210> SEQ ID NO 173
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 173
tgtcacgttc ttgg                                                        14

<210> SEQ ID NO 174
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 174
ctcatctgtc acgt                                                        14

<210> SEQ ID NO 175
<211> LENGTH: 18
<212> TYPE: DNA
<213> ORGANISM: Artificial Sequence
<220> FEATURE:
<223> OTHER INFORMATION: oligonucleotides hybridizing with c-jun

<400> SEQUENCE: 175
cgaagccctc ggcgaacc                                                    18

<210> SEQ ID NO 176
<211> LENGTH: 24
<212> TYPE: DNA
<213> ORGANISM: Artificial Sequence
<220> FEATURE:
<223> OTHER INFORMATION: oligonucleotides hybridizing with c-jun
```

```
<400> SEQUENCE: 176
gcgtgttctg gctgtgcagt tcgg                                          24

<210> SEQ ID NO 177
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 177
ctgccccgtt gacc                                                     14

<210> SEQ ID NO 178
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 178
aggtttgcgt agac                                                     14

<210> SEQ ID NO 179
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 179
ggttgaagtt gctg                                                     14

<210> SEQ ID NO 180
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 180
ctgggttgaa gttg                                                     14

<210> SEQ ID NO 181
<211> LENGTH: 24
<212> TYPE: DNA
<213> ORGANISM: Artificial Sequence
<220> FEATURE:
<223> OTHER INFORMATION: oligonucleotides hybridizing with c-jun

<400> SEQUENCE: 181
tgctggggtt gcgcgggaaa ggcc                                          24

<210> SEQ ID NO 182
<211> LENGTH: 20
<212> TYPE: DNA
<213> ORGANISM: Artificial Sequence
<220> FEATURE:
<223> OTHER INFORMATION: oligonucleotides hybridizing with c-jun

<400> SEQUENCE: 182
tgctgcacgg gcatctgctg                                               20

<210> SEQ ID NO 183
<211> LENGTH: 27
```

```
<212> TYPE: DNA
<213> ORGANISM: Artificial Sequence
<220> FEATURE:
<223> OTHER INFORMATION: oligonucleotides hybridizing with c-jun

<400> SEQUENCE: 183
ggcactgtct gaggctcctc cttcagg                                          27

<210> SEQ ID NO 184
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 184
actccatgtc gatg                                                        14

<210> SEQ ID NO 185
<211> LENGTH: 16
<212> TYPE: DNA
<213> ORGANISM: Artificial Sequence
<220> FEATURE:
<223> OTHER INFORMATION: oligonucleotides hybridizing with c-jun

<400> SEQUENCE: 185
ctctccgcct tgatcc                                                      16

<210> SEQ ID NO 186
<211> LENGTH: 16
<212> TYPE: DNA
<213> ORGANISM: Artificial Sequence
<220> FEATURE:
<223> OTHER INFORMATION: oligonucleotides hybridizing with c-jun

<400> SEQUENCE: 186
gttcctcatg cgcttc                                                      16

<210> SEQ ID NO 187
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 187
ctgagctttc aagg                                                        14

<210> SEQ ID NO 188
<211> LENGTH: 26
<212> TYPE: DNA
<213> ORGANISM: Artificial Sequence
<220> FEATURE:
<223> OTHER INFORMATION: oligonucleotides hybridizing with c-jun

<400> SEQUENCE: 188
gcgattctct ccagcttcct ttttcg                                           26

<210> SEQ ID NO 189
<211> LENGTH: 30
<212> TYPE: DNA
<213> ORGANISM: Artificial Sequence
<220> FEATURE:
<223> OTHER INFORMATION: oligonucleotides hybridizing with c-jun

<400> SEQUENCE: 189
```

```
ctgagctttc aaggttttca cttttccctc                              30
```

<210> SEQ ID NO 190
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 190

```
tccctgagca tgtt                                               14
```

<210> SEQ ID NO 191
<211> LENGTH: 16
<212> TYPE: DNA
<213> ORGANISM: Artificial Sequence
<220> FEATURE:
<223> OTHER INFORMATION: oligonucleotides hybridizing with c-jun

<400> SEQUENCE: 191

```
tctgtttaag ctgtgc                                             16
```

<210> SEQ ID NO 192
<211> LENGTH: 18
<212> TYPE: DNA
<213> ORGANISM: Artificial Sequence
<220> FEATURE:
<223> OTHER INFORMATION: oligonucleotides hybridizing with c-jun

<400> SEQUENCE: 192

```
ctttctgttt aagctgtg                                           18
```

<210> SEQ ID NO 193
<211> LENGTH: 16
<212> TYPE: DNA
<213> ORGANISM: Artificial Sequence
<220> FEATURE:
<223> OTHER INFORMATION: oligonucleotides hybridizing with c-jun

<400> SEQUENCE: 193

```
ggttcatgac tttctg                                             16
```

<210> SEQ ID NO 194
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 194

```
cgtggttcat gact                                               14
```

<210> SEQ ID NO 195
<211> LENGTH: 16
<212> TYPE: DNA
<213> ORGANISM: Artificial Sequence
<220> FEATURE:
<223> OTHER INFORMATION: oligonucleotides hybridizing with c-jun

<400> SEQUENCE: 195

```
actgttaacg tggttc                                             16
```

<210> SEQ ID NO 196
<211> LENGTH: 14
<212> TYPE: DNA
<213> ORGANISM: Artificial Sequence

```
<220> FEATURE:
<223> OTHER INFORMATION: oligonucleotides hybridizing with c-jun

<400> SEQUENCE: 196
ccactgttaa cgtg                                                    14

<210> SEQ ID NO 197
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 197
cccactgtta acgt                                                    14

<210> SEQ ID NO 198
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 198
agcatgagtt ggca                                                    14

<210> SEQ ID NO 199
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 199
gcgttagcat gagt                                                    14

<210> SEQ ID NO 200
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 200
gtttgcaact gctg                                                    14

<210> SEQ ID NO 201
<211> LENGTH: 18
<212> TYPE: DNA
<213> ORGANISM: Artificial Sequence
<220> FEATURE:
<223> OTHER INFORMATION: oligonucleotides hybridizing with c-jun

<400> SEQUENCE: 201
caaaatgttt gcaactgc                                                18

<210> SEQ ID NO 202
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 202
tcgtagaagg tcgt                                                    14
```

```
<210> SEQ ID NO 203
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 203
agggttactg tagc                                                         14

<210> SEQ ID NO 204
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 204
gtagtggtga tgtg                                                         14

<210> SEQ ID NO 205
<211> LENGTH: 14
<212> TYPE: DNA
<213> ORGANISM: Artificial Sequence
<220> FEATURE:
<223> OTHER INFORMATION: oligonucleotides hybridizing with c-jun

<400> SEQUENCE: 205
cgtcgtagaa ggtc                                                         14

<210> SEQ ID NO 206
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 206
cgagaacatc atcg                                                         14

<210> SEQ ID NO 207
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 207
gtagtctgcg ttga                                                         14

<210> SEQ ID NO 208
<211> LENGTH: 20
<212> TYPE: DNA
<213> ORGANISM: Artificial Sequence
<220> FEATURE:
<223> OTHER INFORMATION: oligonucleotides hybridizing with c-fos

<400> SEQUENCE: 208
gctgcagcgg gaggatgacg                                                   20

<210> SEQ ID NO 209
<211> LENGTH: 16
<212> TYPE: DNA
<213> ORGANISM: Artificial Sequence
<220> FEATURE:
<223> OTHER INFORMATION: oligonucleotides hybridizing with c-fos
```

```
<400> SEQUENCE: 209
agtaagagag gctatc                                              16

<210> SEQ ID NO 210
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 210
gtagtaagag aggc                                                14

<210> SEQ ID NO 211
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 211
ggtagtaaga gagg                                                14

<210> SEQ ID NO 212
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 212
gtgagtggta gtaaga                                              16

<210> SEQ ID NO 213
<211> LENGTH: 18
<212> TYPE: DNA
<213> ORGANISM: Artificial Sequence
<220> FEATURE:
<223> OTHER INFORMATION: oligonucleotides hybridizing with c-fos

<400> SEQUENCE: 213
gtccgtgcag aagtcctg                                            18

<210> SEQ ID NO 214
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 214
gaatgaagtt ggcact                                              16

<210> SEQ ID NO 215
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 215
ggaatgaagt tggc                                                14

<210> SEQ ID NO 216
```

```
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 216
gggaatgaag ttgg                                                       14

<210> SEQ ID NO 217
<211> LENGTH: 30
<212> TYPE: DNA
<213> ORGANISM: Artificial Sequence
<220> FEATURE:
<223> OTHER INFORMATION: oligonucleotides hybridizing with c-fos

<400> SEQUENCE: 217
gctgcaccag ccactgcagg tccggactgg                                      30

<210> SEQ ID NO 218
<211> LENGTH: 30
<212> TYPE: DNA
<213> ORGANISM: Artificial Sequence
<220> FEATURE:
<223> OTHER INFORMATION: oligonucleotides hybridizing with c-fos

<400> SEQUENCE: 218
ctggtctgcg atggggccac agaggagacg                                      30

<210> SEQ ID NO 219
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 219
tcatggtctt cacaac                                                     16

<210> SEQ ID NO 220
<211> LENGTH: 30
<212> TYPE: DNA
<213> ORGANISM: Artificial Sequence
<220> FEATURE:
<223> OTHER INFORMATION: oligonucleotides hybridizing with c-fos

<400> SEQUENCE: 220
caatgctctg cgctcggcct cctgtcatgg                                      30

<210> SEQ ID NO 221
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 221
ctagagttcc tcac                                                       14

<210> SEQ ID NO 222
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 222
```

```
gagtacgcta gagt                                                    14

<210> SEQ ID NO 223
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 223
gaagagtacg ctag                                                    14

<210> SEQ ID NO 224
<211> LENGTH: 28
<212> TYPE: DNA
<213> ORGANISM: Artificial Sequence
<220> FEATURE:
<223> OTHER INFORMATION: oligonucleotides hybridizing with c-fos

<400> SEQUENCE: 224
ctgcttccca cccagccccc acattccc                                     28

<210> SEQ ID NO 225
<211> LENGTH: 20
<212> TYPE: DNA
<213> ORGANISM: Artificial Sequence
<220> FEATURE:
<223> OTHER INFORMATION: oligonucleotides hybridizing with c-fos

<400> SEQUENCE: 225
ttcatcctct gtactgggct                                              20

<210> SEQ ID NO 226
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 226
gttacggatg tgca                                                    14

<210> SEQ ID NO 227
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 227
cagttacgga tgtg                                                    14

<210> SEQ ID NO 228
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 228
ccagttacgg atgt                                                    14

<210> SEQ ID NO 229
<211> LENGTH: 14
<212> TYPE: DNA
```

```
<213> ORGANISM: Artificial Sequence
<220> FEATURE:
<223> OTHER INFORMATION: oligonucleotides hybridizing with c-fos

<400> SEQUENCE: 229
agagtctgag ttgg                                                    14

<210> SEQ ID NO 230
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 230
gtgagactca gagt                                                    14

<210> SEQ ID NO 231
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 231
tcttagggtg agac                                                    14

<210> SEQ ID NO 232
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 232
gagagtactt cttagg                                                  16

<210> SEQ ID NO 233
<211> LENGTH: 18
<212> TYPE: DNA
<213> ORGANISM: Artificial Sequence
<220> FEATURE:
<223> OTHER INFORMATION: oligonucleotides hybridizing with c-fos

<400> SEQUENCE: 233
ggaagaaact atgagagt                                                18

<210> SEQ ID NO 234
<211> LENGTH: 18
<212> TYPE: DNA
<213> ORGANISM: Artificial Sequence
<220> FEATURE:
<223> OTHER INFORMATION: oligonucleotides hybridizing with c-fos

<400> SEQUENCE: 234
cttagggaag aaactatg                                                18

<210> SEQ ID NO 235
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 235
cggtaagaaa cttagg                                                  16
```

<210> SEQ ID NO 236
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 236
agcatgcggt aaga                                             14

<210> SEQ ID NO 237
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 237
gtctgaaagc atgc                                             14

<210> SEQ ID NO 238
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 238
agaacaaaga agagcc                                           16

<210> SEQ ID NO 239
<211> LENGTH: 18
<212> TYPE: DNA
<213> ORGANISM: Artificial Sequence
<220> FEATURE:
<223> OTHER INFORMATION: oligonucleotides hybridizing with c-fos

<400> SEQUENCE: 239
caagagaaca aagaagag                                         18

<210> SEQ ID NO 240
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 240
cagcaagaga acaaag                                           16

<210> SEQ ID NO 241
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 241
tcctcagcaa gaga                                             14

<210> SEQ ID NO 242
<211> LENGTH: 14
<212> TYPE: DNA
<213> ORGANISM: Artificial Sequence
<220> FEATURE:

<223> OTHER INFORMATION: oligonucleotides hybridizing with c-fos

<400> SEQUENCE: 242
aggtgtgact tgca                                    14

<210> SEQ ID NO 243
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 243
gaataggtgt gacttg                                  16

<210> SEQ ID NO 244
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 244
cagaataggt gtgact                                  16

<210> SEQ ID NO 245
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 245
gcagaatagg tgtg                                    14

<210> SEQ ID NO 246
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 246
cagttgcaga ataggt                                  16

<210> SEQ ID NO 247
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 247
gaaaccattt ctgacc                                  16

<210> SEQ ID NO 248
<211> LENGTH: 18
<212> TYPE: DNA
<213> ORGANISM: Artificial Sequence
<220> FEATURE:
<223> OTHER INFORMATION: oligonucleotides hybridizing with c-fos

<400> SEQUENCE: 248
tgtgaaacca tttctgac                                18

```
<210> SEQ ID NO 249
<211> LENGTH: 18
<212> TYPE: DNA
<213> ORGANISM: Artificial Sequence
<220> FEATURE:
<223> OTHER INFORMATION: oligonucleotides hybridizing with c-fos

<400> SEQUENCE: 249
cactgtgaaa ccatttct                                                  18

<210> SEQ ID NO 250
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 250
ccactgtgaa acca                                                      14

<210> SEQ ID NO 251
<211> LENGTH: 30
<212> TYPE: DNA
<213> ORGANISM: Artificial Sequence
<220> FEATURE:
<223> OTHER INFORMATION: oligonucleotides hybridizing with c-fos

<400> SEQUENCE: 251
agaactggct cctgcagctt ccctgcttcc                                     30

<210> SEQ ID NO 252
<211> LENGTH: 15
<212> TYPE: DNA
<213> ORGANISM: Artificial Sequence
<220> FEATURE:
<223> OTHER INFORMATION: oligonucleotides hybridizing with c-fos

<400> SEQUENCE: 252
cacctccatt caccc                                                     15

<210> SEQ ID NO 253
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 253
cagtaaaagt gtctgc                                                    16

<210> SEQ ID NO 254
<211> LENGTH: 18
<212> TYPE: DNA
<213> ORGANISM: Artificial Sequence
<220> FEATURE:
<223> OTHER INFORMATION: oligonucleotides hybridizing with c-fos

<400> SEQUENCE: 254
cgacattcag taaaagtg                                                  18

<210> SEQ ID NO 255
<211> LENGTH: 14
<212> TYPE: DNA
<213> ORGANISM: Artificial Sequence
<220> FEATURE:
<223> OTHER INFORMATION: oligonucleotides hybridizing with c-fos
```

<400> SEQUENCE: 255
gaccgacatt cagt                                                    14

<210> SEQ ID NO 256
<211> LENGTH: 18
<212> TYPE: DNA
<213> ORGANISM: Artificial Sequence
<220> FEATURE:
<223> OTHER INFORMATION: oligonucleotides hybridizing with c-fos

<400> SEQUENCE: 256
cttctggaga taactaga                                                18

<210> SEQ ID NO 257
<211> LENGTH: 18
<212> TYPE: DNA
<213> ORGANISM: Artificial Sequence
<220> FEATURE:
<223> OTHER INFORMATION: oligonucleotides hybridizing with c-fos

<400> SEQUENCE: 257
catcttattc ctttccct                                                18

<210> SEQ ID NO 258
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 258
cagccatctt attcct                                                  16

<210> SEQ ID NO 259
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 259
tgcagccatc ttattc                                                  16

<210> SEQ ID NO 260
<211> LENGTH: 15
<212> TYPE: DNA
<213> ORGANISM: Artificial Sequence
<220> FEATURE:
<223> OTHER INFORMATION: oligonucleotides hybridizing with c-fos

<400> SEQUENCE: 260
gagtgtatca gtcag                                                   15

<210> SEQ ID NO 261
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 261
ggagtgtatc agtc                                                    14

<210> SEQ ID NO 262
<211> LENGTH: 16

<212> TYPE: DNA
<213> ORGANISM: Artificial Sequence
<220> FEATURE:
<223> OTHER INFORMATION: oligonucleotides hybridizing with c-fos

<400> SEQUENCE: 262
cttggagtgt atcagt                                                   16

<210> SEQ ID NO 263
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 263
acagagtacc tacc                                                     14

<210> SEQ ID NO 264
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 264
ccaactttcc cttaag                                                   16

<210> SEQ ID NO 265
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 265
ccttatgctc aatctc                                                   16

<210> SEQ ID NO 266
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 266
gtcttactca aggg                                                     14

<210> SEQ ID NO 267
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 267
acagtcttac tcaagg                                                   16

<210> SEQ ID NO 268
<211> LENGTH: 18
<212> TYPE: DNA
<213> ORGANISM: Artificial Sequence
<220> FEATURE:
<223> OTHER INFORMATION: oligonucleotides hybridizing with c-fos

<400> SEQUENCE: 268

```
cataagacac agtcttac                                              18

<210> SEQ ID NO 269
<211> LENGTH: 18
<212> TYPE: DNA
<213> ORGANISM: Artificial Sequence
<220> FEATURE:
<223> OTHER INFORMATION: oligonucleotides hybridizing with c-fos

<400> SEQUENCE: 269
gaaagcataa gacacagt                                              18

<210> SEQ ID NO 270
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 270
ggaaagcata agacac                                                16

<210> SEQ ID NO 271
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 271
agggataaag gaaagc                                                16

<210> SEQ ID NO 272
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 272
cctgtataca gagg                                                  14

<210> SEQ ID NO 273
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 273
tgtctcctgt atacag                                                16

<210> SEQ ID NO 274
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 274
catcttctag ttggtc                                                16

<210> SEQ ID NO 275
<211> LENGTH: 16
<212> TYPE: DNA
<213> ORGANISM: Artificial Sequence
```

```
<220> FEATURE:
<223> OTHER INFORMATION: oligonucleotides hybridizing with c-fos

<400> SEQUENCE: 275
ctcatcttct agttgg                                                    16

<210> SEQ ID NO 276
<211> LENGTH: 18
<212> TYPE: DNA
<213> ORGANISM: Artificial Sequence
<220> FEATURE:
<223> OTHER INFORMATION: oligonucleotides hybridizing with c-fos

<400> SEQUENCE: 276
cttctcatct tctagttg                                                  18

<210> SEQ ID NO 277
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 277
caaagcagac ttctca                                                    16

<210> SEQ ID NO 278
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 278
ctgcaaagca gact                                                      14

<210> SEQ ID NO 279
<211> LENGTH: 18
<212> TYPE: DNA
<213> ORGANISM: Artificial Sequence
<220> FEATURE:
<223> OTHER INFORMATION: oligonucleotides hybridizing with c-fos

<400> SEQUENCE: 279
ctagtttttc cttctcct                                                  18

<210> SEQ ID NO 280
<211> LENGTH: 18
<212> TYPE: DNA
<213> ORGANISM: Artificial Sequence
<220> FEATURE:
<223> OTHER INFORMATION: oligonucleotides hybridizing with c-fos

<400> SEQUENCE: 280
tctagttttt ccttctcc                                                  18

<210> SEQ ID NO 281
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 281
caggatgaac tctagt                                                    16
```

```
<210> SEQ ID NO 282
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 282
cgagaacatc atgg                                                       14

<210> SEQ ID NO 283
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 283
gtagtaggaa aggc                                                       14

<210> SEQ ID NO 284
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 284
ggtagtagga aagg                                                       14

<210> SEQ ID NO 285
<211> LENGTH: 14
<212> TYPE: DNA
<213> ORGANISM: Artificial Sequence
<220> FEATURE:
<223> OTHER INFORMATION: oligonucleotides hybridizing with c-fos

<400> SEQUENCE: 285
ggaatggtag tagg                                                       14

<210> SEQ ID NO 286
<211> LENGTH: 15
<212> TYPE: DNA
<213> ORGANISM: Artificial Sequence
<220> FEATURE:
<223> OTHER INFORMATION: oligonucleotides hybridizing with c-fos

<400> SEQUENCE: 286
ggtcattgag aagag                                                      15

<210> SEQ ID NO 287
<211> LENGTH: 16
<212> TYPE: DNA
<213> ORGANISM: Artificial Sequence
<220> FEATURE:
<223> OTHER INFORMATION: oligonucleotides hybridizing with c-fos

<400> SEQUENCE: 287
gctaatgttc ttgacc                                                     16

<210> SEQ ID NO 288
<211> LENGTH: 15
<212> TYPE: DNA
<213> ORGANISM: Artificial Sequence
<220> FEATURE:
<223> OTHER INFORMATION: oligonucleotides hybridizing with MIA
```

```
<400> SEQUENCE: 288
gtcaggaatc ggcag                                              15

<210> SEQ ID NO 289
<211> LENGTH: 16
<212> TYPE: DNA
<213> ORGANISM: Artificial Sequence
<220> FEATURE:
<223> OTHER INFORMATION: oligonucleotides hybridizing with MIA

<400> SEQUENCE: 289
cttggagaag acatac                                             16

<210> SEQ ID NO 290
<211> LENGTH: 14
<212> TYPE: DNA
<213> ORGANISM: Artificial Sequence
<220> FEATURE:
<223> OTHER INFORMATION: oligonucleotides hybridizing with MIA

<400> SEQUENCE: 290
tgcctcccca gaag                                               14

<210> SEQ ID NO 291
<211> LENGTH: 17
<212> TYPE: DNA
<213> ORGANISM: Artificial Sequence
<220> FEATURE:
<223> OTHER INFORMATION: oligonucleotides hybridizing with MIA

<400> SEQUENCE: 291
cactggcagt agaaatc                                            17

<210> SEQ ID NO 292
<211> LENGTH: 15
<212> TYPE: DNA
<213> ORGANISM: Artificial Sequence
<220> FEATURE:
<223> OTHER INFORMATION: oligonucleotides hybridizing with MIA

<400> SEQUENCE: 292
gctcactggc agtag                                              15

<210> SEQ ID NO 293
<211> LENGTH: 14
<212> TYPE: DNA
<213> ORGANISM: Artificial Sequence
<220> FEATURE:
<223> OTHER INFORMATION: oligonucleotides hybridizing with MIA

<400> SEQUENCE: 293
atggtcagga atcg                                               14

<210> SEQ ID NO 294
<211> LENGTH: 16
<212> TYPE: DNA
<213> ORGANISM: Artificial Sequence
<220> FEATURE:
<223> OTHER INFORMATION: oligonucleotides hybridizing with MIA

<400> SEQUENCE: 294
gaatggtcag gaatcg                                             16

<210> SEQ ID NO 295
```

```
<211> LENGTH: 14
<212> TYPE: DNA
<213> ORGANISM: Artificial Sequence
<220> FEATURE:
<223> OTHER INFORMATION: oligonucleotides hybridizing with MIA

<400> SEQUENCE: 295
catcgtggac tgtg                                                      14

<210> SEQ ID NO 296
<211> LENGTH: 14
<212> TYPE: DNA
<213> ORGANISM: Artificial Sequence
<220> FEATURE:
<223> OTHER INFORMATION: oligonucleotides hybridizing with MIA

<400> SEQUENCE: 296
agccatggag atag                                                      14

<210> SEQ ID NO 297
<211> LENGTH: 15
<212> TYPE: DNA
<213> ORGANISM: Artificial Sequence
<220> FEATURE:
<223> OTHER INFORMATION: oligonucleotides hybridizing with MIA

<400> SEQUENCE: 297
cagccatgga gatag                                                     15

<210> SEQ ID NO 298
<211> LENGTH: 16
<212> TYPE: DNA
<213> ORGANISM: Artificial Sequence
<220> FEATURE:
<223> OTHER INFORMATION: oligonucleotides hybridizing with MIA

<400> SEQUENCE: 298
acagccatgg agatag                                                    16

<210> SEQ ID NO 299
<211> LENGTH: 17
<212> TYPE: DNA
<213> ORGANISM: Artificial Sequence
<220> FEATURE:
<223> OTHER INFORMATION: oligonucleotides hybridizing with MIA

<400> SEQUENCE: 299
cacagccatg gagatag                                                   17

<210> SEQ ID NO 300
<211> LENGTH: 16
<212> TYPE: DNA
<213> ORGANISM: Artificial Sequence
<220> FEATURE:
<223> OTHER INFORMATION: oligonucleotides hybridizing with MIA

<400> SEQUENCE: 300
ccacagccat ggagat                                                    16

<210> SEQ ID NO 301
<211> LENGTH: 14
<212> TYPE: DNA
<213> ORGANISM: Artificial Sequence
<220> FEATURE:
<223> OTHER INFORMATION: oligonucleotides hybridizing with MIA

<400> SEQUENCE: 301
```
gccatggaga tagg                                              14

<210> SEQ ID NO 302
<211> LENGTH: 15
<212> TYPE: DNA
<213> ORGANISM: Artificial Sequence
<220> FEATURE:
<223> OTHER INFORMATION: oligonucleotides hybridizing with MIA

<400> SEQUENCE: 302
agccatggag atagg                                             15

<210> SEQ ID NO 303
<211> LENGTH: 16
<212> TYPE: DNA
<213> ORGANISM: Artificial Sequence
<220> FEATURE:
<223> OTHER INFORMATION: oligonucleotides hybridizing with MIA

<400> SEQUENCE: 303
cagccatgga gatagg                                            16

<210> SEQ ID NO 304
<211> LENGTH: 17
<212> TYPE: DNA
<213> ORGANISM: Artificial Sequence
<220> FEATURE:
<223> OTHER INFORMATION: oligonucleotides hybridizing with MIA

<400> SEQUENCE: 304
acagccatgg agatagg                                           17

<210> SEQ ID NO 305
<211> LENGTH: 14
<212> TYPE: DNA
<213> ORGANISM: Artificial Sequence
<220> FEATURE:
<223> OTHER INFORMATION: oligonucleotides hybridizing with MIA

<400> SEQUENCE: 305
catggagata gggt                                              14

<210> SEQ ID NO 306
<211> LENGTH: 15
<212> TYPE: DNA
<213> ORGANISM: Artificial Sequence
<220> FEATURE:
<223> OTHER INFORMATION: oligonucleotides hybridizing with MIA

<400> SEQUENCE: 306
catggagata gggtg                                             15

<210> SEQ ID NO 307
<211> LENGTH: 16
<212> TYPE: DNA
<213> ORGANISM: Artificial Sequence
<220> FEATURE:
<223> OTHER INFORMATION: oligonucleotides hybridizing with MIA

<400> SEQUENCE: 307
catggagata gggtgg                                            16

<210> SEQ ID NO 308
<211> LENGTH: 14
<212> TYPE: DNA

```
<213> ORGANISM: Artificial Sequence
<220> FEATURE:
<223> OTHER INFORMATION: oligonucleotides hybridizing with MIA

<400> SEQUENCE: 308
atggagatag ggtg                                                       14

<210> SEQ ID NO 309
<211> LENGTH: 15
<212> TYPE: DNA
<213> ORGANISM: Artificial Sequence
<220> FEATURE:
<223> OTHER INFORMATION: oligonucleotides hybridizing with MIA

<400> SEQUENCE: 309
atggagatag ggtgg                                                      15

<210> SEQ ID NO 310
<211> LENGTH: 16
<212> TYPE: DNA
<213> ORGANISM: Artificial Sequence
<220> FEATURE:
<223> OTHER INFORMATION: oligonucleotides hybridizing with MIA

<400> SEQUENCE: 310
atggagatag ggtggc                                                     16

<210> SEQ ID NO 311
<211> LENGTH: 17
<212> TYPE: DNA
<213> ORGANISM: Artificial Sequence
<220> FEATURE:
<223> OTHER INFORMATION: oligonucleotides hybridizing with MIA

<400> SEQUENCE: 311
atggagatag ggtggct                                                    17

<210> SEQ ID NO 312
<211> LENGTH: 14
<212> TYPE: DNA
<213> ORGANISM: Artificial Sequence
<220> FEATURE:
<223> OTHER INFORMATION: oligonucleotides hybridizing with MIA

<400> SEQUENCE: 312
ggagataggg tggc                                                       14

<210> SEQ ID NO 313
<211> LENGTH: 15
<212> TYPE: DNA
<213> ORGANISM: Artificial Sequence
<220> FEATURE:
<223> OTHER INFORMATION: oligonucleotides hybridizing with MIA

<400> SEQUENCE: 313
ggagataggg tggct                                                      15

<210> SEQ ID NO 314
<211> LENGTH: 14
<212> TYPE: DNA
<213> ORGANISM: Artificial Sequence
<220> FEATURE:
<223> OTHER INFORMATION: oligonucleotides hybridizing with MIA

<400> SEQUENCE: 314
gaaatagccc aggc                                                       14
```

-continued

```
<210> SEQ ID NO 315
<211> LENGTH: 15
<212> TYPE: DNA
<213> ORGANISM: Artificial Sequence
<220> FEATURE:
<223> OTHER INFORMATION: oligonucleotides hybridizing with MIA

<400> SEQUENCE: 315
gaaatagccc aggcg                                                     15

<210> SEQ ID NO 316
<211> LENGTH: 17
<212> TYPE: DNA
<213> ORGANISM: Artificial Sequence
<220> FEATURE:
<223> OTHER INFORMATION: oligonucleotides hybridizing with MIA

<400> SEQUENCE: 316
gaaatagccc aggcgag                                                   17

<210> SEQ ID NO 317
<211> LENGTH: 14
<212> TYPE: DNA
<213> ORGANISM: Artificial Sequence
<220> FEATURE:
<223> OTHER INFORMATION: oligonucleotides hybridizing with MIA

<400> SEQUENCE: 317
ggaaatagcc cagg                                                      14

<210> SEQ ID NO 318
<211> LENGTH: 15
<212> TYPE: DNA
<213> ORGANISM: Artificial Sequence
<220> FEATURE:
<223> OTHER INFORMATION: oligonucleotides hybridizing with MIA

<400> SEQUENCE: 318
ggaaatagcc caggc                                                     15

<210> SEQ ID NO 319
<211> LENGTH: 14
<212> TYPE: DNA
<213> ORGANISM: Artificial Sequence
<220> FEATURE:
<223> OTHER INFORMATION: oligonucleotides hybridizing with MIA

<400> SEQUENCE: 319
gtcttcacat cgac                                                      14

<210> SEQ ID NO 320
<211> LENGTH: 15
<212> TYPE: DNA
<213> ORGANISM: Artificial Sequence
<220> FEATURE:
<223> OTHER INFORMATION: oligonucleotides hybridizing with MIA

<400> SEQUENCE: 320
gtcttcacat cgact                                                     15

<210> SEQ ID NO 321
<211> LENGTH: 16
<212> TYPE: DNA
<213> ORGANISM: Artificial Sequence
<220> FEATURE:
```

```
<223> OTHER INFORMATION: oligonucleotides hybridizing with MIA

<400> SEQUENCE: 321
gtcttcacat cgactt                                                    16

<210> SEQ ID NO 322
<211> LENGTH: 17
<212> TYPE: DNA
<213> ORGANISM: Artificial Sequence
<220> FEATURE:
<223> OTHER INFORMATION: oligonucleotides hybridizing with MIA

<400> SEQUENCE: 322
gtcttcacat cgacttt                                                   17

<210> SEQ ID NO 323
<211> LENGTH: 18
<212> TYPE: DNA
<213> ORGANISM: Artificial Sequence
<220> FEATURE:
<223> OTHER INFORMATION: oligonucleotides hybridizing with MIA

<400> SEQUENCE: 323
gtcttcacat cgactttg                                                  18

<210> SEQ ID NO 324
<211> LENGTH: 18
<212> TYPE: DNA
<213> ORGANISM: Artificial Sequence
<220> FEATURE:
<223> OTHER INFORMATION: oligonucleotides hybridizing with MIA

<400> SEQUENCE: 324
gtcttcacat cgactttg                                                  18

<210> SEQ ID NO 325
<211> LENGTH: 18
<212> TYPE: DNA
<213> ORGANISM: Artificial Sequence
<220> FEATURE:
<223> OTHER INFORMATION: oligonucleotides hybridizing with MIA

<400> SEQUENCE: 325
ccatttgtct gtcttcac                                                  18
```

DOSAGE OF OLIGONUCLEOTIDES SUITABLE FOR THE TREATMENT OF TUMORS

BACKGROUND

1. Field

The present disclosure is directed to the use of an oligonucleotide for the preparation of a pharmaceutical composition suitable for intravenous administration for the prevention and/or treatment of tumors that are modulated by TGF-beta 1, TGF-beta 2, TGF-beta 3, VEGF, interleukin 10, c-jun, c-fos, MIA, and/or prostaglandin E2.

2. Discussion of the Background Art

Pancreatic carcinoma is one of the most aggressive human tumors. It is almost uniformly fatal and one of the leading causes of cancer-related death in the Western world. It is more common in males than in females. In most countries, the incidence ranges from 8 to 12 cases per 100 000, with a marked increase in Japan in the last few years. The lack of clinical symptoms usually leads to a diagnosis at a late stage of the disease. At the time of diagnosis, 85% of the patients have a locally advanced, non-resectable (stage II or stage III) or even metastatic (stage IV) carcinoma, with extra-pancreatic spread to distant organs such as liver or lung. Most patients succumb to the tumor's propensity to metastasize and its instrinsic resistance to cytotoxic agents and radiotherapy (Van Cutsem et al., 2007). Less than 3% of the patients are still alive 5 years after diagnosis despite receiving every available therapy. Pancreatic carcinoma is accompanied by severe clinical symptoms such as cachexia, pain, obstructive jaundice, and wasting, requiring intensive supportive care.

The available treatment options are scarce. Since pancreatic carcinomas are not very sensitive to chemotherapy, therapeutic agents such as 5-FU (5-fluorouracil), gemcitabine and oxaliplatin may alleviate symptoms, but the median survival is only 6 months. Gemcitabine has been widely accepted as the gold standard chemotherapy treatment, showing a median survival of about 6 months and a 1-year survival rate of about 20% (Burris et al., 1997). The tyrosine kinase inhibitor erlotinib, which targets epidermal-growth-factor-receptor (EGFR), was approved recently for first-line treatment of locally advanced, unresectable or metastatic pancreatic cancer in combination with gemcitabine monotherapy (Moore et al., 2007).

Another type of cancer is the malignant melanoma, which is formed by melanocytes and occurs primarily in the skin, metastasizing rapidly throughout the body. Ultraviolet damage, immunosuppression, and congenital nevi are the predominant risk factors. The occurrence of this deadliest of all skin cancers has dramatically increased over the last few years, with the highest incidence found in Australia and New Zealand. Median survival for advanced stages (distant metastases) is 7 to 8 months, depending on the organ sites affected, and the 5-year survival rate is less than 5% (Young et al., 2006). An increased level of TGF-beta is expressed in all metastatic melanomas and in 94% of deeply invasive primary melanomas (Reed et al., 1994).

In principal, all melanoma lesions, including lymph nodes, are removed surgically. Radiotherapy provides symptomatic relief. When metastases are present, (adjuvant) chemotherapy such as nitrosureas or dacarbazine is the first choice, although rarely with curative potential and no improvement of survival. The response rate is with 10 to 20% rather modest and short-lived, with a response duration of about 3 months. The addition of high-dose interferon-alpha (IFN-alpha) or PEGylated IFN-alpha as immunotherapy enhances response rates, but does not influence the overall survival and involves substantial side effects. Similar findings appear to treatment with interleukin-2 (IL-2) with an even higher toxicity.

Colorectal carcinoma is a leading cause of morbidity and mortality. 5-year survival rates for stage III and IV are 67% and 10%, respectively (SEER 2004). The highest incidence rates of colorectal cancer are found in North America, Australia/New Zealand, Western Europe, and Japan with 30.1 to 49.3 per 100,000 for men and 20.1 to 36.0 for women.

Surgery is the primary treatment for colorectal carcinoma, and adjuvant chemo-, immuno-, or radiotherapy can be added, with the FOLFOX-regimen being the first line of care. The advent of agents such as capecitabine, irinotecan, and oxaliplatin as well as targeted agents such as cetuximab, erlotinib, and bevacizumab brought prolongation of survival to the treatment of colorectal carcinoma patients. Patients with metastatic disease, treated with such novel targeted therapies, can expect a median survival approaching 2 years (Kallinowski 2005), although with some severe side effects such as diarrhea, nausea, hemorrhages and bleeding, rash, allergic reactions, and heart problems with concomitant additional management cost. Despite this progress, 5-year survival rates are still very low for stage IV patients with 10% (SEER Program 2004), and the medical need for better treatment options is high. Multiple ongoing clinical trials are testing several combinations of chemotherapy and targeted therapies that mainly target EGFR and VEGF, with the aim to optimize current treatment. Other agents include those that inhibit the activity of the non-receptor tyrosine kinases, whereby both approaches are not specific enough on their own.

Hence, there is an urgent need for the improvement of tumor therapy, which may be reached with new compounds, combination of known compounds, or a variation of the dosage of compounds. An overall feature of pharmaceutical substances is their increasing efficacy accompanied by an increase in amounts being administered. Particular substances used in tumor therapy show a strong correlation between the total amount administered and the inhibition of tumor growth.

Additionally, cellular uptake is a limiting factor for the efficacy of "in vivo" administration of oligonucleotides, where conventionally high concentrations and high amounts of oligonucleotides are administered to inhibit the production of the respective protein.

Nevertheless, the clinical success of these substances is limited, since an increase in the concentration and the total amount of these substances, which can be administered to a mammal suffering from tumor metastases, nerval disease and immunosuppression, is correlated with a strong increase in severe side effects and toxicity.

EP 1 008 649 and EP 0 695 354 teach that oligonucleotides hybridizing with the mRNA of TGF-beta 1 and/or TGF-beta 2 can be used for manufacturing pharmaceutical compositions. EP 1 089 764 further teaches that inhibitors of substances negatively affecting the immune system in combination with oligonucleotides hybridizing with the mRNA of TGF-beta, VEGF, interleukin 10, and prostaglandin E2 and their respective receptors can be used for manufacturing a pharmaceutical composition as well. But these patents offer a wide range of concentrations in which the oligonucleotides can be administered. WO 2006/117400 A2 specifies dosages of oligonucleotides, which are used for the preparation of a pharmaceutical composition for preventing and/or treating cancer, and wherein the oligonucleotide is suitable for local administration in low concentrations.

Similar to its function in high-grade glioma, TGF-beta (-1, -2, and/or -3) appears to play a central role in malignancy and progression of pancreatic carcinoma (Friess et al., 1993; von Berstorff, et al., 2001), malignant melanoma (Reed et al., 1994), and colorectal carcinoma, respectively. Given the limited progress achieved in the treatment of pancreatic carcinoma, malignant melanoma, and colorectal carcinoma in recent years, the need for more effective therapies in terms of prolonged survival is obvious.

A solution to this problem is provided by the present disclosure described in the following, which is directed to a method of preventing and/or treating a tumor with an oligonucleotide comprising 8 to 30 nucleotide building blocks, which hybridizes with mRNA of TGF-beta 1, -2, -3, VEGF, interleukin-10, c-jun, c-fos, MIA, and/or prostaglandin E2 wherein the antisense oligonucleotide is administered intravenously or subcutaneously.

SUMMARY OF THE DISCLOSURE

A pharmaceutical composition containing at least one oligonucleotide, which is administered intravenously or subcutaneously, is effective in the treatment of tumors and metastases, respectively, in particular of pancreatic carcinoma, malignant melanoma, or colorectal carcinoma, leading to a prolongation of survival compared to common pharmaceuticals.

That at least one oligonucleotide for the prevention and/or treatment of diseases that are modulated by TGF-beta 1, TGF-beta 2, TGF-beta 3, VEGF, interleukin-10, c-jun, c-fos, MIA, and/or prostaglandin E2 disclosure has a length of about 8 to about 30 nucleotide building blocks.

In particular, the antisense oligonucleotide, which hybridizes with mRNA of TGF-beta 1, -2, and/or -3, and which is used in the method for preventing and/or treating a tumor, is administered intravenously in a dose of 40 mg/m$^2$/d to 190 mg/m$^2$/d.

Surprisingly, already a low dose and a low total amount, respectively, of the pharmaceutical composition and the antisense oligonucleotide, respectively, for example a total amount of 400 to 800 mg/m$^2$/treatment cycle, is more efficient than higher doses or total amounts of the pharmaceutical composition and the antisense oligonucleotide, respectively.

Each dose may be administered for one or more days forming cylces of administration of different duration, for example 1 day to 12 weeks. Administration free intervals follow the administration cycles, wherein these intervals are always of the same time period or vary between the administration cycles. Preferably, the pharmaceutical composition is administered in a cycle of 7 days followed by a 7-day treatment free period, or alternatively in a cycle of 4 days followed by a 10-day treatment free period.

Unexpectedly, already a low dose of 80 mg/m$^2$/d in a 7 d treatment cycle as well as a low dose of 140 mg/m$^2$/d or 190 mg/m$^2$/d in a 4 d treatment cycle showed high efficiency in the prolongation of survival of tumor patients.

Further advantages of the disclosure are enhanced affinity for nucleic acid target, enhanced cellular uptake, enhanced safety, less side effects, and increased stability in the presence of nucleases.

BRIEF DESCRIPTION OF THE DRAWINGS

FIGS. 1A-1D present preferred sequences of oligonucleotides hybridizing with TGF-beta 1 (SEQ ID NO. 1 to 21), TGF-beta 2 (SEQ ID NO. 22 to 48), TGF-beta 3 (SEQ ID NO. 49 to 77), prostaglandin E2 (SEQ ID NO. 78 to 89), VEGF (SEQ ID NO. 90 to 126), interleukin-10 (SEQ ID NO. 127 to 146), c-jun (SEQ ID NO. 147 to 205), c-fos (SEQ ID NO. 206 to 287), and/or MIA (SEQ ID NO. 288 to 325).

DETAILED DESCRIPTION OF THE PREFERRED EMBODIMENT

Figure 2A:
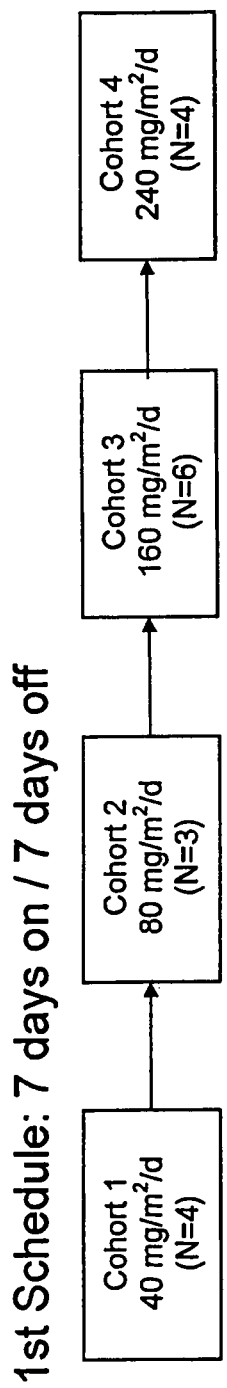
FIGS. 2A-2C show a first treatment schedule comprising four cohorts of patients, wherein a pharmaceutical composition comprising an antisense oligonucleotide of SEQ ID NO. 22 is administered in a dose of 40 mg/m$^2$/d, 80 mg/m$^2$/d, 160 mg/m$^2$/d or 240 mg/red for 7 days (one cycle) followed by a 7-day treatment free period, and a second treatment schedule comprising the administration of a pharmaceutical composition comprising an antisense oligonucleotide of SEQ ID NO. 22 in a dose of 140 mg/m$^2$/d, 190 mg/m$^2$/d, 250 mg/m$^2$/d, or 330 mg/m$^2$/d for 4 days (one cycle) followed by a 10-days treatment free period.
Figure 2B:
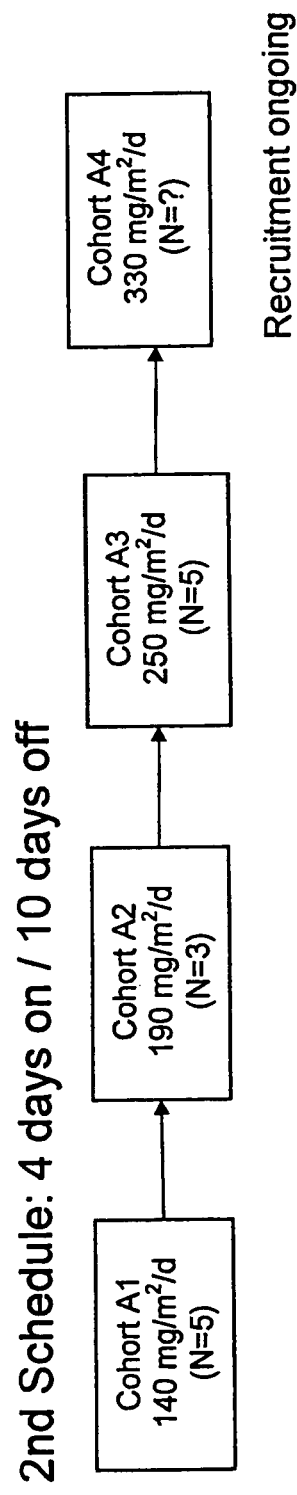
Figure 2C:
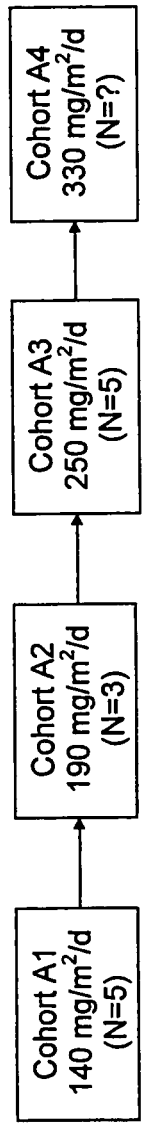

The expression about in the context of this disclosure comprises deviations from the absolute value given in the text from 0 to 100%, more preferred from 1 to 80%, even more preferred from 2 to 60%, more preferred from 3 to 40%, more preferred from 4 to 20%, and even more preferred from 5 to 10% of the respective value.

Adverse event in the context of this disclosure is understood as any untoward medical occurrence in a patient or clinical investigation subject after the administration of a pharmaceutical preparation that does not necessarily have a causal relationship with the treatment of the respective pharmaceutical preparation. An adverse event can therefore be any unfavourable and unintended sign (including an abnormal laboratory finding), symptom, or disease e.g. due to disease progression. Another expression for adverse event is symptom.

Pancreatic or colorectal tumor, used synonymously with tumor of the pancreas or the colorectum, or malignant melanoma according to this disclosure is any tumor of the pancreas, colorectum or skin including metastases, metastases derived from other parts of the pancreas, colorectum or skin or derived from any other tumor in the body.

In the present disclosure the expression tumor comprises any benign or malignant tumor of a human or animal body.

Hybridizing in the context of this disclosure implies, that two nucleotide chains at least partly form a double strand by hydrogen bonding. The double strand develops completely when the two nucleotide chains have exact antisense sequences. But even if any nucleotide of an oligonucleotide, also referred to as nucleotide building block is substituted by another nucleotide, the respective nucleotide is modified or even when a spacer is in the place of the respective oligonucleotide, the oligonucleotide can still hybridize with the target molecule, generally the mRNA of a protein, and with this inhibit the production of said protein.

Metastasis in the context of this disclosure means that at least one cell separates or dissociates from a tumor tissue and moves via e.g. the lymphatic system, the blood vessels, and/or invading the surrounding tissue to another part of the body of a mammal, preferably a human, where it settles down and forms new tumor tissue.

The term oligonucleotide of the disclosure encompasses any pharmaceutically acceptable salt, ester, or any other compound that upon administration to a mammal is capable of providing the biologically active metabolite or residue thereof. This is accomplished by specific hybridization of the compounds with one or more nucleic acids encoding TGF-beta 1, TGF-beta 2, TGF-beta 3, VEGF, interleukin 10, c-jun, c-fos, MIA, and/or prostaglandin E2. The term oligonucleotide comprises for example an antisense oligonucleotide, siRNA, miRNA or an aptamer.

The terms nucleic acids and oligonucleotides are used synonymously in the context of this disclosure.

In some embodiments, the nucleic acids are not antisense nucleic acids, meaning that they do not function by binding partly or completely to complementary DNA or RNA species, in particular genomic DNA or RNA species, within a cell and thereby inhibiting the function of said DNA or RNA species, in particular genomic DNA or RNA species.

In one embodiment the oligonucleotide of this disclosure also comprises the oligonucleotide as described in the patents EP 0 695 354 and EP 1 008 649 as well as those of the international patent applications published under No. WO 01/68146, WO 98/33904, WO 99/63975 and WO 99/63975.

Oligonucleotides hybridizing with TGF-beta in one preferred embodiment include at least one sequence set forth as SEQ ID Nos: 1 to 78, or of SEQ ID Nos 79 to 89, or of SEQ ID Nos 90 to 126, or of 127 to 146, or of SEQ ID Nos 147 to 205, or of SEQ ID Nos 206 to 287, or of 287 to 325.

Oligonucleotides or nucleic acids may include oligonucleotides having non-naturally occurring portions with similar function. Naturally occurring nucleotides as well as non-naturally occurring nucleotides, modifications and spacers are also referred to as nucleotide building block. The most common nucleotide building block is a nucleotide. Modified or substituted nucleotides as well as spacers are also comprised by the expression nucleotide building block.

These modified or substituted oligonucleotides are often preferred over native forms because of desirable properties such as enhanced cellular uptake, enhanced affinity for nucleic acid target (e.g. protein), altered intracellular localization and increased stability in the presence of nucleases. Modifications of the oligonucleotides as used herein comprise any chemical modification of the sugar, the base moiety and/or the internucleotide linkage.

In one embodiment, the ring structure of the ribose group of the nucleotides in the modified oligonucleotide or polynucleotide has oxygen in the ring structure substituted with N—H, N—R (with R being an alkyl, more preferred alkyl with 1 to 20 carbons, very preferred alkyls are methyl, ethyl, propyl, isopropyl, butyl, isobutyl, or R is an aryl substituent), S and/or methylene.

Pharmaceutical preparation in the context of this disclosure comprises an oligonucleotide of this disclosure within a pharmaceutically acceptable carrier.

In one embodiment, nucleic acids or oligonucleotides with a covalently modified base and/or sugar include for example nucleic acids having backbone sugars, which are covalently attached to low molecular weight organic groups other than a hydroxyl group at the 3' and/or 2' position or a phosphate group at the 5' position. Thus, modified nucleic acids may additionally include at least one 2'-O-substituted ribose group. For purposes of this disclosure, the term "2'-substituted" means substitution of the 2'-OH of the ribose molecule. The O may be substituted with N, S and the substituent can further comprise an alkyl with 1 to 20 carbons e.g. O-alkyl, S-alkyl, NH-alkyl, N-dialkyl, O-aryl, S-aryl, NH-aryl, O-aralkyl, S-aralkyl, and NH-aralkyl. Preferred embodiments of 2'-O-alkyl-groups may be methoxy-, ethoxy-, propyloxy-, isopropyloxy-, and methoxy-ethoxy. Further modifications of nucleotide building blocks are also given by patents U.S. Pat. No. 6,143,881, U.S. Pat. No. 5,591,721, U.S. Pat. No. 5,652,355, U.S. Pat. No. 5,962,425, U.S. Pat. No. 5,969,116 and U.S. Pat. No. 5,914,396. Another preferred embodiment is a nucleotide building block, comprising at least one deoxyribose with an alkyl-group bound to the 2'-carbon. The alkyl may have about 1 to about 30 carbons, 1 to about 20 carbons, 1 to about 10 carbons, or 1 to about 5 carbons. Preferred alkyl-groups are ethyl-, propyl-, isopropyl-, butyl-group, highly preferred is the methyl-group.

In yet another embodiment, modified nucleic acids may include sugars such as arabinose instead of ribose. Thus the nucleic acids may be heterogeneous in backbone composition thereby containing any possible combination of polymer units linked together such as peptide-nucleic acids (which have amino acid backbone linked to nucleic acid bases). In some embodiments the nucleic acids may be homogeneous in backbone composition.

The substituted purines and pyrimidines of the nucleic acids may include standard purines and pyrimidines such as cytosine as well as base analogs such as substituted bases (Wagner et al. 1993). Purines and pyrimidines include, but are not limited to adenine, cytosine, guanine, thymine, inosin, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties.

The single nucleotides in each oligonucleotide may contain the same modifications, may contain combinations of these modifications, or may combine these modifications with phosphodiester linkages. Methods of rendering oligonucleotide nuclease resistant may include, but are not limited to, covalently modifying the purine or pyrimidine bases. For example, bases may be methylated, hydroxymethylated, or otherwise substituted (e.g., glycosylated) such that the oligonucleotides or polynucleotides are rendered substantially acid and nuclease resistant.

In a preferred embodiment, at least one end of the oligonucleotide is a biotin, biotin analog, avidin, or avidin analog. These molecules have the ability to block the degradation of the protected oligonucleotide and provide means for high affinity attachment of the modified nucleic acids to the solid support. Avidin and biotin derivatives, which can be used to prepare the reagents of this disclosure, include streptavidin, succinylated avidin, monomeric avidin, biocytin (biotin-epsilon-N-lysine), biocytin hydrazide, amine or sulfhydryl derivatives of 2-iminobiotin and biotinyl-epsilon-aminocaproic acid hydrazide. Additional biotin derivatives, such as biotin-N-hydroxysuccinimide ester, biotinyl-epsilon-aminocaproic acid-N-hydroxysuccinimide ester, sulfosuccinimidyl 6-(biotin amido)hexanoate, N-hydroxysuccinimideiminobiotin, biotinbromoacetylhydrazide, p-diazobenzoyl biocytin and 3-(N-maleimidopropionyl)-biocytin, can also be used as end-blocking groups on the oligonucleotides of the present disclosure.

In a further preferred embodiment, the oligonucleotide is conjugated with a polymer, in particular PEG, at the 3'- and/or 5'-end of the oligonucleotide and/or at any internal nucleotide of the oligonucleotide as described in WO 2008/077956 A2.

In yet another embodiment, the base units are maintained for hybridization with an appropriate nucleic acid target compound. One such oligomeric compound, an oligonucleotide mimetic that has been shown to have excellent hybridization properties, may be referred to as a peptide nucleic acid (PNA). In PNA compounds, the sugar-backbone of an oligonucleotide is replaced with an amide containing backbone, in particular an aminoethylglycine backbone. The nucleobases are bound directly or indirectly to aza nitrogen atoms of the amide portion of the backbone. Representative United States patents that teach the preparation of PNA compounds include, but are not limited to, U.S. Pat. Nos. 5,539,082, 5,714,331, and 5,719,262. Further teaching of PNA compounds can be found in Nielsen et al. 1991.

Further backbone modified oligonucleotide may include, for example, phosphorothioates, chiral phosphorothioates, phosphorodithioates, phosphorotriesters, aminoalkylphosphorotriesters, methyl- and other alkyl-phosphonates including 3'-alkylene phosphonates and chiral phosphonates, phosphinates, phosphoramidates, including 3'-aminophosphoramidate and aminoalkylphosphoramidates, thiono-phosphor-amidates, thionoalkylphosphonates, thionoalkylphosphotriesters, and boranophosphates having normal 3'-5' linkages, 2'-5' linked analogs of these, and those having inverted polarity, wherein the adjacent pairs of nucleoside units are linked 3'-5' to 5'-3' or 2'-5' to 5'-2'. Various salts, mixed salts, and free acid forms are also included. One preferred embodiment is the sodium salt of the nucleic acid.

In some embodiments at least one nucleotide of an oligonucleotide is modified as described in one of the modifications above. The modification can either cover the oligonucleotide continuously or irregularly.

In yet another embodiment, at least two modifications as described above are combined within one oligonucleotide.

In another embodiment, 1 to about 12 or 1 to about 8 or 1 to about 4 or 1 to about 2 oligonucleotides and/or nucleotide linkages at the 3' and/or 5'end of the oligonucleotide are modified as described above.

In one embodiment the oligonucleotide of this disclosure hybridizes with a target, e.g. TGF-beta or its subtypes more preferred TGF-beta 1, TGF-beta 2, and/or TGF-beta 3. The antisense structure of the mRNA of the targets is described in PCT/EP2004/053604.

Chain elongation means that oligonucleotides of the sequence listing and other oligonucleotides, that have additional nucleotides of the sequence of the respective antisense structure of the mRNA of said targets, are still within the scope of this disclosure. The additional nucleotides in one embodiment are according to the coding region of the mRNA, in yet another embodiment, the additional nucleotides are also from the non-coding part of the mRNA, including introns and exons. The additional nucleotides may comprise about 1 to about 10,000 nucleotides, about 1 to about 5,000 nucleotides, about 1 to about 3,000 nucleotides, about 1 to about 1,000 nucleotides, about 1 to about 500 nucleotides, about 1 to about 100 nucleotides, about 1 to about 50 nucleotides, about 1 to about 25 nucleotides, about 1 to about 10 nucleotides, about 1 to about 5 nucleotides or about 1 to about 2 nucleotides bound to at least one of the 3' and/or 5' end, in another embodiment, to at least one of the 2' or 5'end. In yet another embodiment, some nucleotide building blocks of these oligonucleotides or polynucleotides may be modified or substituted by spacers and/or modifications as described herein.

Pharmaceutically acceptable salts refer to physiologically and pharmaceutically acceptable salts of the compounds used in the disclosure, which means that the salts retain the biological activities of the parent compounds without undesired toxicological effects.

In one embodiment the oligonucleotide or its active derivative is a single stranded oligonucleotide, in yet another embodiment the oligonucleotide is double stranded, which means that the oligonucleotide is hybridized completely or partly with a second oligonucleotide that has about 50% to about 100% of the exact antisense structure of said oligonucleotide. This may result in a double strand, in which both oligonucleotides hybridize with less bond strength or in double strand with overlapping ends. The two oligonucleotides might have the same length, in other words they have the same amount of nucleotide building blocks or their length might differ, also resulting in overlapping ends on one or both ends.

The expression spacer in the context of this disclosure comprises any nucleotide building block, which is not obviously a derivative or a modification of a nucleotide, but connects two nucleotide building blocks in a way, that the resulting oligonucleotide still hybridizes with its target, e.g. mRNA of TGF-beta 1, TGF-beta 2, TGF-beta 3, prostaglandin E2, c-fos, c-jun, MIA, or interleukin-10.

One embodiment of the disclosure refers to a method for preventing and/or treating a tumor, said method comprising intravenously administering an oligonucleotide in an amount of between about 400 to about 800 mg/m2/treatment cycle, said antisense oligonucleotide comprises 8 to 30 nucleotide building blocks, which hybridizes with mRNA of TGF-beta 1, -2 and/or -3 for the preparation of a pharmaceutical composition. The antisense oligonucleotide is administered intravenously in a dose of 80 mg/m$^2$/d, 140 mg/m$^2$/d or 190 mg/m$^2$/d, preferably for a prolongation of survival of at least 0.5 to 40 months, of at least 1 to 40 months, or of at least 3 to 40 months.

In other embodiments of the disclosure, the oligonucleotide may be administered in a dose of 10 mg/m$^2$/d to 500 mg/m$^2$/d, preferably in a dose of 40 mg/m$^2$/d to 400 mg/m$^2$/d, more preferred in a dose of 40 mg/m$^2$/d to 250 mg/m$^2$/d, 80 mg/m$^2$/d to 250 mg/m$^2$/d, 140 mg/m$^2$/d to 250 mg/m$^2$/d, 160 mg/m$^2$/d to 250 mg/m$^2$/d, 190 mg/m$^2$/d to 250 mg/m$^2$/d, or 40 mg/m$^2$/d to 190 mg/m$^2$/d, 80 mg/m$^2$/d to 190 mg/m$^2$/d, 160 mg/m$^2$/d to 190 mg/m$^2$/d, or 40 mg/m$^2$/d to 160 mg/m$^2$/d, 80 mg/m$^2$/d to 160 mg/m$^2$/d, or even more preferred in a dose of 40 mg/m$^2$/d to 140 mg/m$^2$/d, 80 mg/m$^2$/d to 140 mg/m$^2$/d. The most preferred doses of the oligonucleotide are 20 mg/m$^2$/d, 40 mg/m$^2$/d, 60 mg/m$^2$/d, 80 mg/m$^2$/d, 100 mg/m$^2$/d, 120 mg/m$^2$/d, 140 mg/m$^2$/d, 160 mg/m$^2$/d, 180 mg/m$^2$/d, 190 mg/m$^2$/d, 200 mg/m$^2$/d, 210 mg/m$^2$/d, 220 mg/m$^2$/d, 230 mg/m²/d, 240 mg/m²/d, 250 mg/m²/d, 300 mg/m²/d, 350 mg/m²/d, 400 mg/m²/d, 450 mg/m²/d, or 500 mg/m²/d.

In a preferred embodiment an oligonucleotide may be administered in a dose of 40 mg/m²/d, 80 mg/m²/d, 140 mg/m²/d, 160 mg/m²/d, 190 mg/m²/d, 240 mg/m²/d, 250 mg/m²/d, 300 mg/m²/d, 330 mg/m²/d, or 350 mg/m²/d.

In another embodiment of the disclosure, the pharmaceutical composition and the antisense oligonucleotide in the above mentioned doses, respectively, prolongs survival of a patient suffering from a malignant tumor such as pancreatic carcinoma, malignant melanoma, or colorectal carcinoma for at least or about 0.5 to 60 months, 0.5 to 48 months, 0.5 to 36 months, 0.5 to 24 months, 0.5 to 12 months, 0.5 to 9 months, 0.5 to 6 months, or at least or about 1 to 60 months, 1 to 48 months, 1 to 36 months, 1 to 24 months, 1 to 12 months, 1 to 9 months, 1 to 6 months, preferably at least or about 2 to 60 months, 2 to 48 months, 2 to 36 months, 2 to 24 months, 2 to 12 months, 2 to 9 months, 2 to 6 months, more preferred at least or about 3 to 60 months, 3 to 48 months, 3 to 36 months, 3 to 24 months, 3 to 12 months, 3 to 9 months, even more preferred for at least or about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 months, most preferred for at least 10 years, 15 years, 20 years, 25 years, 30 years, 35 years, 40 years, 45 years, 50 years, 55 years, 60 years, 65 years, 70 years, 75 years, 80 years, 85 years, 90 years, 95 years, or 100 years.

Whereas the oligonucleotides of this disclosure are single stranded, in some embodiments at least parts of the single-stranded nucleic acid are double-stranded. Double-stranded molecules are more stable in vivo, while single-stranded molecules have increased activity.

In one embodiment the oligonucleotide has a length between about 8 to about 30 nucleotides and is complementary to the mRNA of the targets TGF-beta 1, TGF-beta 2, TGF-beta 3, VEGF, interleukin 10, c-jun, c-fos, MIA, and prostaglandin E2. In more preferred embodiments the oligonucleotides of this disclosure have lengths of about 7 to about 25 nucleotides, of about 8 to about 30 nucleotides, even more preferred of about 12 to 18 nucleotides. Preferred embodiments of oligonucleotides usable in this disclosure are shown in the sequence listing under SEQ ID NOs 1 to 78, very preferred embodiments are SEQ ID Nos 22 to 48, even more preferred is SEQ ID Nos 1 or 22 or 58. In one preferred embodiment SEQ ID No 22 is administered in the form of its sodium salt having a molecular weight of 6142.4 g, respectively 7115.3 g as hydrate, comprising about 54 molecules of crystal water per oligonucleotide.

Other oligonucleotides usable in pharmaceutical preparations according to this disclosure are oligonucleotides described in the sequence listing, respectively, the examples of EP 1 089 764, EP 0 695 534, PCT/EP98/00497 and PCT/EP2005/002101.

In other embodiments the at least one oligonucleotide for the manufacturing of a pharmaceutical preparation comprises at least one phosphorothioate linkage between two nucleotide building blocks. The phosphorothioate linkage may cover 0%-5%, 5% to 10%, 10% to 15%, 15% to 20%, 20% to 25%, 25% to 30%, 30% to 35%, 35% to 40%, 40% to 45%, 45% to 50%, 50% to 55%, 55% to 60%, 60% to 65%, 65% to 70%, 70% to 75%, 75% to 80%, 80% to 85%, 85% to 90%, 90% to 95% or 95% to 100% of the linkages. The phosphorothioate linkages may be scattered regularly or irregularly over the oligonucleotide. In some embodiments the phosphorothioate is accumulated at either one or both of the 3' and/or 5' ends of the oligonucleotide. Another preferred embodiment is an oligonucleotide where all linkages between the nucleotides are phosphorothioates.

In one embodiment the oligonucleotide is a single strand oligonucleotide. Single strand means, that all oligonucleotide building blocks are in one line and do not hybridize with a second oligonucleotide or antisense oligonucleotide and are not bound otherwise.

In a preferred embodiment the pharmaceutical composition and the oligonucleotide, respectively, is administered intravenously, or by infusion into a tissue, a tumor or a body cavity. In more preferred embodiments the tissue is selected from the group of bile duct, bladder, bone, bone marrow, brain, breast, colon, endometrium, epithelium, gall bladder, head, head and neck, heart, intestine, joints, kidney, larynx, liver, lung, lymphatic node, lymphatic vessels, muscle, oesophagus, ovary, pancreas, prostate, rectum, urinary duct, skin and its layers, spleen, stomach, testis, thymus, thyroid, tonsil, or uterus and/or is administered to the respective tumor of this tissue.

In another embodiment the pharmaceutical preparation of oligonucleotides is administered into a body cavity, selected from the group of bile duct, bladder, colon, gall bladder, joint cavity, pleural cavity, intraperitoneal space, the rectum, the intestinal tract, the urinary duct, the urinary bladder, and the ventricular space.

In yet other embodiments of this disclosure the pharmaceutical composition comprising at least one oligonucleotide is administered for example intravenously with a flow rate of about 0.01 to about 1 ml/h, 0.01 to about 10 ml/h, about 0.1 ml/h to about 1 mL/h, about 0.1 ml/h to about 10 mL/h, 1 mL/h to 10 mL/h, or 5 mL/h to 10 mL/h. Further preferred are flow rates of about 0.2 mL/min to about 9 mL/min, 0.3 mL/h to 8 mL/h, 0.4 mL/h to 7 mL/h, 0.5 mL/h to 6 mL/h, 0.6 mL/h to 5 mL/h, 0.7 mL/h to 5 mL/h, 0.8 mL/h to 5 mL/h, 0.9 mL/h to 5 mL/h, more preferred of about 0.1 mL/h, 0.2 mL/h, 0.3 mL/h, 0.4 mL/h, 0.5 mL/h, 0.6 mL/h, 0.7 mL/h, 0.8 mL/h, 0.9 mL/h, 1.0 mL/h, 1.1 mL/h, 1.2 mL/h, 1.3 mL/h, 1.4 mL/h, 1.5 mL/h, 1.6 mL/h, 1.7 mL/h, 1.8 mL/h, 1.9 mL/h, or 2.0 mL/h.

In one embodiment, the pharmaceutical composition is administered with an application system such as a syringe. A preferred application system comprises a portable pump, connected with flexible tubes to a port system. The port system is connected to an infusion catheter. Application systems usable for this disclosure are for example described in the international patent application PCT/EP 2004/004211.

Preferably, the total volume per day of the pharmaceutical composition and the oligonucleotide, respectively, which is administered for example intravenously ranges from about 1 mL/d to about 500 mL/d, about 2 mL/d to about 250 mL/d, more preferred from about 5 mL/d to about 200 mL/d, even more preferred from about 7 mL/d to about 150 mL/d, even more preferred from about 10 mL/d to about 100 mL/d, even more preferred from about 15 mL/d to about 50 mL/d, and most preferred from about 20 mL/d or about 50 mL/d.

In one embodiment the pharmaceutical composition and the oligonucleotide, respectively, is administered for example intravenously or into a tumor, a tissue or a body cavity in 1 to 100 cycles, 1 to 50 cycles, 1 to 25 cycles, 1 to 20 cycles, 1 to 15 cycles, 1 to 10 cycles, preferably in 2 to 10 cycles, 2 to 8 cycles, 2 to 6 cycles, or 2 to 4 cycles, more preferably in 1, 2, 3, 4, 5, 6, 7, 8, 9, 10, 11, 12, 13, 14, 15, 16, 17, 18, 19, 20, 21, 22, 23, 24, or 25 cycles, which are administered in one or more days and the duration of each cycle is identical or varies.

In a preferred embodiment, the pharmaceutical composition and the antisense oligonucleotide, respectively, is administered in at least or about 5 h, 10 h, 15 h, 20 h, 24 h, 36 h, 2d, 3d, 4d, 5d, 6d, 7d, 8d, 9d, 10d, 11d, 12d, 13d, 14d, 15d, 3 weeks, 4 weeks, 5 weeks, 6 weeks, 7 weeks, 8 weeks, 9 weeks, 10 weeks, 11 weeks, or 12 weeks. More preferred, the pharmaceutical composition and the antisense oligonucleotide, respectively, is suitable to be administered for example intravenously in at least or about 5 h, 10 h, 15 h, 20 h, 1 d, 36 h, 2 d, 3 d, 4 d, 5 d, 6 d, 7 d, 8 d, 9 d, 10 d, 11 d, 12 d, 13 d, 14 d, 15 d, 3 weeks, 4 weeks, 5 weeks, 7 weeks, 8 weeks, 9 weeks, 10 weeks, 11 weeks, or 12 weeks as one treatment cycle, wherein the pharmaceutical composition and the antisense oligonucleotide, respectively, may be administered in consecutive days, every second day, every third day, every forth day, every fifth day, every sixth day, every seventh day, in consecutive weeks, every second week, every third week, every forth week, every fifth week, every sixth week, every seventh week, every eighth week, every nineth week, every tenth week, every eleventh week, or every twelfth week.

In preferred embodiments, the time interval between one treatment cycle and another cycle is at least or about 5 h, 10 h, 15 h, 20 h, 24 h, 36 h, 2 d, 3 d, 4 d, 5 d, 6 d, 7 d, 8 d, 9 d, 10 d, 11 d, 12 d, 13 d, 14 d, 15 d, 3 weeks, 4 weeks, 5 weeks, 7 weeks, 8 weeks, 9 weeks, 10 weeks, 11 weeks, or 12 weeks, wherein the time intervals between the treatment cycles are either identical or vary. During these time intervals between the administration cycles, no pharmaceutical composition and antisense oligonucleotide, respectively, is administered. Alternatively, during the time intervals between the administration cycles another compound such as a chemotherapeutic, for example 5-fluorouracil, BCNU, or a vinca alkaloid, is administered.

Figure 3:
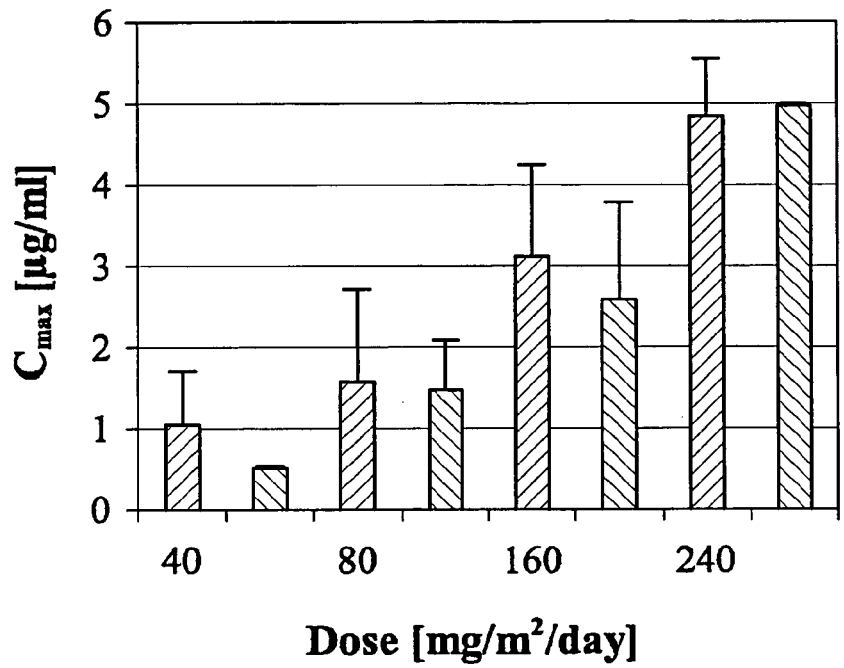
FIG. 3 presents the dose dependency of $C_{max}$ in plasma of patients who had received an oligonucleotide in two cycles of the same dose (mg/m$^2$) for 7 days. The patients were not treated for 7 days in between these treatment cycles. Different patients were treated with different doses of the antisense oligonucleotide. Black columns show the result of the first treatment cycle, grey columns show the results of the second treatment cycle.
Figure 4:
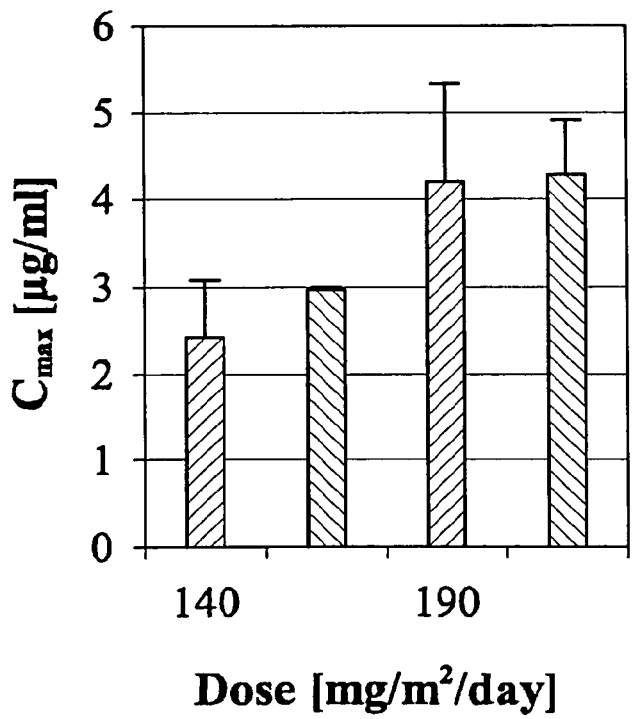
FIG. 4 shows the dose dependency of $C_{max}$ in plasma of patients who had received an oligonucleotide in two cycles of the same dose (mg/m$^2$) for 4 days. The patients were not treated for 10 days in between these treatment cycles. Different patients were treated with different doses of the antisense oligonucleotide. Black columns show the result of the first treatment cycle, grey columns show the results of the second treatment cycle.

In one embodiment the bioavailability of the administered oligonucleotide in a cell or in plasma of a subject, unexpectedly increases with a decrease in the duration of the treatment cycle, if the same total amount of the oligonucleotide is administered. The concentration of the oligonucleotide in the cell or the plasma of a patient increases with increasing dose of the administered oligonucleotide independent of the duration of the treatment cycle (FIGS. 3 and 4). $C_{max}$ is defined as the maximal concentration of a substance in a medium, and indicates in FIGS. 3 and 4 the maximal concentration of an antisense oligonucleotide, in particular a TGF-beta 2 antisense oligonucleotide in the blood plasma of a subject.

Figure 5:
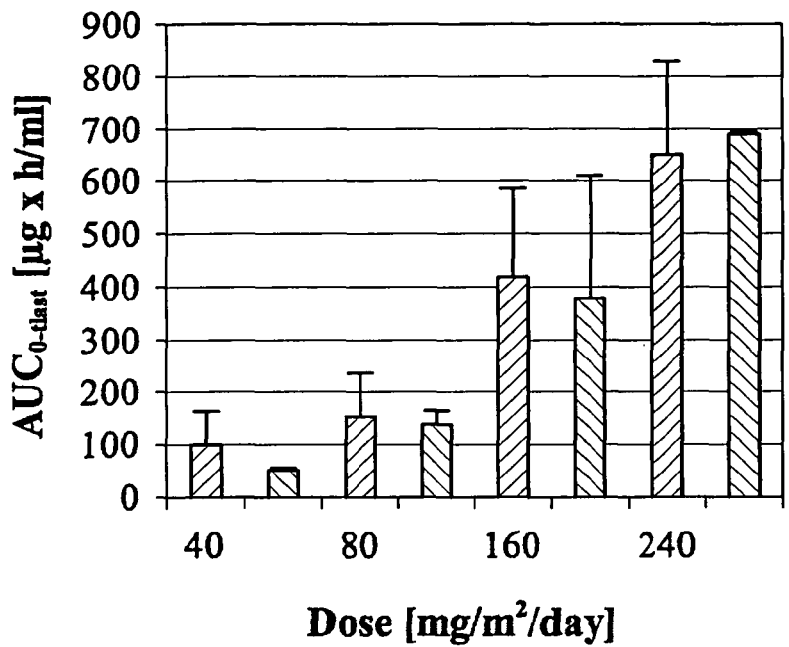
FIG. 5 demonstrates the dose dependency of the AUC in plasma of patients who had received an oligonucleotide in two cycles of the same dose (mg/m$^2$) for 7 days. The patients were not treated for 7 days inbetween these treatment cycles. Different patients were treated with different doses of the antisense oligonucleotide. Black columns show the result of the first treatment cycle, grey columns show the results of the second treatment cycle.
Figure 6:
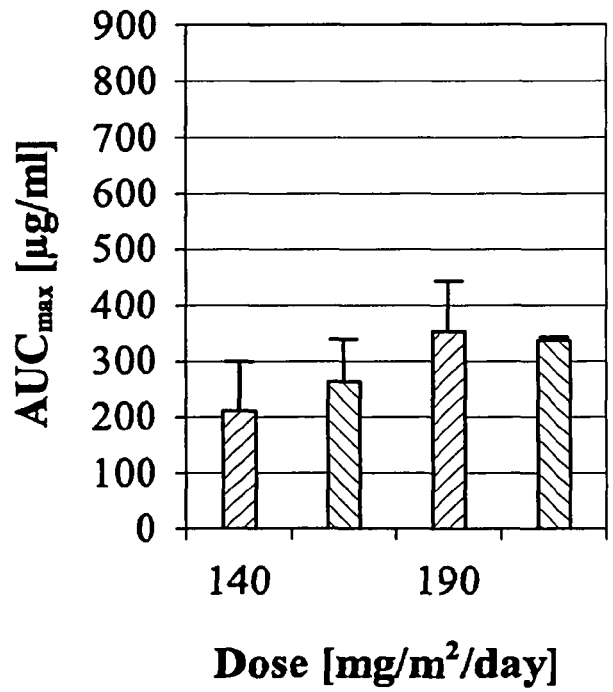
FIG. 6 presents the dose dependency of the AUC in plasma of patients who had received an oligonucleotide in two cycles of the same dose (mg/m$^2$) for 4 days. The patients were not treated for 10 days inbetween these treatment cycles. Different patients were treated with different doses of the antisense oligonucleotide. Black columns show the result of the first treatment cycle, grey columns show the results of the second treatment cycle.

In a preferred embodiment, an increasing dose of the oligonucleotide results in an increase of the bioavailability of this oligonucleotide in a cell or plasma of a subject, wherein the same total amount of an oligonucleotide results in a higher bioavailability, if the duration of the treatment cycle is reduced (FIGS. 5 and 6). Bioavailability is a measurement of the extent of a therapeutically active drug, for example an antisense oligonucleotide that reaches the systemic circulation and is available at the site of action. Bioavailability is analysed by the AUC (area under the curve), which is defined as the area under the curve of the plasma concentration in a determined time period, e.g., in Example 6 four or seven days.

In a most preferred embodiment, the antisense oligonucleotide, for example dissolved in a physiological (i.e., isotonic) solution, may be administered in at least or about 1 or 2 to 50 cycles, in 1 or 2 to 40 cycles, 1 or 2 to 30 cycles, 1 or 2 to 20 cycles, 1 or 2 to 10 cycles, 1 or 2 to 8 cycles, 1 or 2 to 6 cycles, 1 or 2 to 4 cycles, 1 or 2 cycles, wherein one cycle consists of 4 d and the time interval between the cycles is 10 d, or wherein one cycle consists of 4 d and the time interval between the cycles is 7 d, or wherein one cycle consists of 10 d and the time interval between the cycles is 4 d, or wherein one cycle consists of 7 d and the time interval between the cycles is 7 d, or wherein one cycle consists of 7 d and the time interval between the cycles is 10 d, or wherein one cycle consists of 10 d and the time interval between the cycles is 7 d wherein the tumor is preferably pancreatic carcinoma, malignant melanoma, or colorectal carcinoma.

The pharmaceutical composition and the antisense oligonucleotide, respectively, may be administered in a total amount of at least or about 150 to 5 000 mg/m$^2$/cycle, of 150 to 4 500 mg/m$^2$/cycle, of 150 to 4 000 mg/m$^2$/cycle, of 150 to 3 500 mg/m$^2$/cycle, of 150 to 3 000 mg/m$^2$/cycle, of 150 to 2 500 mg/m$^2$/cycle, of 150 to 2 000 mg/m$^2$/cycle, of 150 to 1 500 mg/m$^2$/cycle, of 150 to 1 000 mg/m$^2$/cycle, of 150 to 500 mg/m$^2$/cycle, or 150 to 250 mg/m$^2$/cycle, more preferred of at least or about 300, 400, 500, 600, 700, 800, 900 or 1000 mg/m$^2$/cycle, and most preferred of at least or about 510, 520, 530, 540, 550, 560, 570, 580, or 590 mg/m$^2$/cycle.

Most surprising of the present disclosure is that not the highest dose and amount, respectively, of the antisense oligonucleotide shows the best effects or that the treatment effects increase with an increased dose of the antisense oligonucleotide, but that lower amounts of for example 560 mg/m$^2$/cycle present the best effects in the treatment of tumors (see examples of the disclosure).

The pharmaceutical composition and the antisense oligonucleotide, respectively, may be used as a first line treatment, i.e, without any tumor therapy in advance, as a second line treatment, i.e., with one tumor therapy in advance, as a third line treatment, i.e., with two tumor therapies in advance, or as a fourth line treatment, i.e., with three tumor therapies in advance, or as at least a fifth line treatment with at least four tumor therapies in advance, wherein the preceding tumor therapy is for example a chemotherapy or a radiotherapy.

In yet another embodiment the pharmaceutical composition comprises at least one oligonucleotide and in addition at least one further adjuvant treatment. For more details about adjuvants, also referred to as immunostimulants, see EP 1 089 764. In a preferred embodiment the adjuvant is an oligonucleotide comprising an CpG-motive. For further details about CpG motives see Krieg 2002.

Preferred embodiments of the pharmaceutical composition of this disclosure are used in mammals, where the preferred embodiment of mammal is a human. Besides being useful in human treatment, the present disclosure is also useful for other subjects including veterinary animals, exotic animals and farm animals, including mammals, rodents, and the like. Mammals include humans, horses, dogs, pigs, cats, or primates (for example, a monkey, a chimpanzee, or a lemur). Rodents include rats, mice, squirrels, or guinea pigs.

Pharmaceutical compositions include fluid pharmaceutical compositions containing the oligonucleotide in a concentration of at least or about 1 mM to about 25 M, 1 mM to about 20 M, 1 mM to about 10 M, 1 mM to about 5 M, 1 mM to about 1 M. In another preferred embodiment the pharmaceutical composition may contain the oligonucleotide concentration of at least or about 10 mM, 20 mM, 30 mM, 40 mM, 50 mM, 60 mM, 70 mM, 80 mM, 90 mM or 100 mM to about 150 mM, 200 mM, 250 mM, 300 mM, 350 mM, 400 mM, 450 mM, 500 mM, 550 mM, 600 mM, 650 mM, 700 mM, 750 mM, 800 mM, 850 mM, 900 mM, 950 mM, 1 M, 2, M, 3 M, 4 M, 5 M, 6 M, 7 M, 8 M, 9 M, 10 M, 11 M, 12 M, 13 M, 14 M, 15 M, 16 M, 17 M, 18 M, 19 M, or 20 M.

The pharmaceutical composition may include sterile aqueous solutions that may also contain buffers, diluents and other suitable additives, such as, but not limited to, penetration enhancers, acceptable carriers or excipients. The term pharmaceutical composition implies that the liquids or substances of this composition are pure and/or combined with pharmaceutically acceptable carriers.

The term pharmaceutically acceptable carrier means one or more compatible liquid fillers, diluents or encapsulating substances that can be administered to a human or other mammal. The term "carrier" denotes an organic or inorganic ingredient, natural or synthetic, with which the active ingredient may be combined to facilitate the application. The components of the pharmaceutical composition are capable of being combined with the oligonucleotides of the present disclosure without negatively influencing the desired pharmaceutical efficacy. Such carriers enable the oligonucleotides of the disclosure to be formulated as liquids, gels, syrups, slurries, suspensions, or emulsions.

As described above the pharmaceutical compositions may also include microcapsules, nanocapsules, micro- and nanospheres, and suspensions, oligonucleotides coated onto microscopic gold particles or preparations with protracted release of oligonucleotides, in whose preparation excipients and additives and/or auxiliaries such as disintegrants, binders, coating agents, swelling agents, lubricants, or solubilizers are customarily used. For the infusion into the stomach, intestine, colon, or rectum for example an enema is useful. For a brief review of present methods of drug delivery, see Langer (1990).

In yet another embodiment, a suspension of the compounds is prepared as appropriate oily infusion. Suitable lipophilic solvents or vehicles include fatty oils such as sesame oil, or synthetic fatty acid esters, such as ethyl oleate or triglycerides, or liposomes. Aqueous infusion suspensions comprise substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions.

In yet another embodiment, the oligonucleotides may be in powder form for reconstitution with a suitable vehicle, e.g., sterile pyrogen-free water, before use. In other embodiments the oligonucleotide is reconstituted with an isotonic solution. Isotonic solution is any aqueous solution with an osmotic pressure as high as the osmotic pressure of the body. Commonly used are solutions of salts, sugars and so on. In preferred embodiments the isotonic solution is a 0.9% sodium chloride solution or a Ringer-lactate solution (e.g., DAB7).

In yet another embodiment, the active compounds, e.g., the oligonucleotide, may be in form of a concentrate for dilution with a suitable vehicle, e.g., sterile pyrogen-free water, before use. In yet another embodiment, the compounds are formulated in rectal or vaginal compositions such as suppositories or retention enemas or tablets, e.g., containing conventional suppository bases such as cocoa butter or other glycerides.

In yet another embodiment, the compounds are formulated as a depot preparation. In one embodiment such long acting preparations are formulated with suitable polymeric or hydrophobic materials (for example, as an emulsion in an acceptable oil) or ion exchange resins, or as sparingly slow soluble derivatives, for example as a sparingly slow soluble salt.

In other embodiments, delivery systems include time-release, delayed release, or sustained release delivery systems. Such systems can avoid repeated administrations of the compounds, thereby providing increasing convenience to the subject and the physician. Many types of release delivery systems are available and known to those of ordinary skill in the art.

In one embodiment, the delivery systems include polymer based systems such as poly(lactide-glycolide), copolyoxalates, polycaprolactones, polyesteramides, polyorthoesters, polyhydroxybutyric acid, and polyanhydrides, more preferred polyanhydrides with molecular weight of more than 20,000 Da. In one preferred embodiment the polyanhydride is a polycondensation of dicarbonic acids with high molecular weight. More details see also EP 0 260 415. Microcapsules of the foregoing polymers containing drugs are described for example in U.S. Pat. No. 5,075,109.

In another embodiment, improvement of oligonucleotide uptake has been achieved with different systems of vectorization including liposomes (neutral, cationic, immunoliposome), micro- and nanoparticles, polymers, or covalent attachment to a carrier (Lefebure et al., 1995). Lipid-mediated transfection has also been used to deliver oligonucleotides (Wang and Martini, 1996). In another embodiment the delivery systems include non-polymer systems that are, e.g., lipids including sterols such as cholesterol, cholesterol esters and fatty acids or neutral fats such as mono-, di- and triglycerides, hydrogel release systems, silastic systems, peptide based systems, and the like.

Specific examples include, but are not limited to: (a) erosional systems, in which an agent of the disclosure is contained in a form within a matrix such as those described in U.S. Pat. Nos. 4,452,775, 4,675,189, and 5,736,152, and (b) diffusional systems, in which an active component permeates at a controlled rate from a polymer such as described in U.S. Pat. Nos. 3,854,480, 5,133,974 and 5,407,686.

In still other embodiments, the oligonucleotides are formulated with GELFOAM®, a commercial product consisting of modified collagen fibers that degrade slowly.

In one embodiment, the pharmaceutical compositions also comprise suitable solid or gel phase carriers or excipients. Examples of such carriers or excipients include, but are not limited to calcium carbonate, calcium phosphate, various sugars, starches, cellulose derivatives, gelatin, and polymers such as polyethylene glycols.

In one embodiment, the oligodeoxynucleotides are administered neat or in the form of a pharmaceutically acceptable salt. The salts have to be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic acid. Also, such salts can be prepared as alkaline metal or alkaline earth salts, such as sodium, potassium or calcium salts of the carboxylic acid group.

In another embodiment, the pharmaceutical composition further comprises at least one buffer and/or at least one preservative. In one embodiment suitable buffering agents include but are not limited to acetic acid and a salt (e.g., 1-2% w/v), citric acid and a salt (e.g., 1-3% w/v), boric acid and a salt (e.g., 0.5-2.5% w/v), and phosphoric acid and a salt (e.g., 0.8-2% w/v). Suitable preservatives include benzalkonium chloride (e.g., 0.003-0.03% w/v), chlorobutanol (e.g., 0.3-0.9% w/v), parabens (e.g., 0.01-0.25% w/v), and thiomersal (e.g., 0.004-0.02% w/v).

In yet another embodiment the pharmaceutical compositions may also include penetration enhancers in order to enhance the alimentary delivery. Penetration enhancers may be classified as belonging to one of five broad categories, i.e., fatty acids, bile salts, chelating agents, surfactants, and non-surfactants (Lee et al., 1991; Muranishi, 1990). One or more penetration enhancers from one or more of these broad categories may be included.

Various fatty acids and their derivatives, which act as penetration enhancers, may include, for example, oleic acid, lauric acid, capric acid, myristic acid, palmitic acid, stearic acid, linoleic acid, linolenic acid, dicaprate, tricaprate, recinleate, monoolein (1-monooleoyl-rac-glycerol), dilaurin, caprylic acid, araichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., 1991; Muranishi, 1990; El-Hariri et al., 1992). Examples of some presently preferred fatty acids are sodium caprate and sodium laurate, used singly or in combination at concentrations of for example 0.5 to 5%.

The physiological roles of bile include the facilitation of dispersion and absorption of lipids and fat-soluble vitamins (Brunton, 1996). Various natural bile salts, and their synthetic derivatives, act as penetration enhancers. Thus, the term "bile salt" includes any of the naturally occurring components of bile as well as any of their synthetic derivatives. A presently preferred bile salt is chenodeoxycholic acid (CDCA) (Sigma Chemical Company, St. Louis, Mo.), used in concentrations of for example 0.5 to 2%.

Complex formulations comprising one or more penetration enhancers may be used. For example, bile salts may be used in combination with fatty acids to produce complex formulations. Preferred combinations include CDCA combined with sodium caprate or sodium laurate (e.g., 0.5 to 5%).

In one embodiment, additionally chelating agents are used that include, but are not limited to, disodium ethylenediaminetetraacetate (EDTA), citric acid, salicylates (e.g., sodium salicylate, 5-methoxysalicylate and homovanillate), N-acyl derivatives of collagen, laureth-9 and N-amino acyl derivatives of beta-diketones (enamines) (Lee et al., 1991; Muranishi, 1990; Buur et al. 1990). Chelating agents have the added advantage of also serving as DNase inhibitors.

In yet another embodiment additionally surfactants are used. Surfactants include, for example, sodium lauryl sulphate, polyoxyethylene-9-lauryl ether and polyoxyethylene-20-cetyl ether (Lee et al., 1991), and perfluorochemical emulsions such as FC-43 (Takahashi et al., 1988).

Non-surfactants include, for example, unsaturated cyclic ureas, 1-alkyl- and 1-alkenylazacyclo-alkanone derivatives (Lee et al., 1991), and non-steroidal anti-inflammatory agents such as diclofenac sodium, indomethacin, and phenylbutazone (Yamashita et al., 1987).

In one embodiment, the pharmaceutical composition of the present disclosure additionally contains other adjunct components conventionally found in pharmaceutical compositions, at their art-established usage levels. Thus, for example, the compositions may contain additional compatible pharmaceutically active materials such as, e.g., antipruritics, astringents, local anesthetics or anti-inflammatory agents, or may contain additional materials useful in physically formulating various dosage forms of the composition of present disclosure, such as dyes, flavoring agents, preservatives, antioxidants, opacifiers, thickening agents, and stabilizers. However, such materials, when added, should not unduly interfere with the biological activities of the components of the compositions of the disclosure.

EXAMPLES

In these examples the results of systemic toxicity studies as well as clinical studies in patients are reported. All these studies have been performed in accordance with current Good Clinical Practice (GCP) guidelines and have been approved by local ethics committees. Patient studies furthermore have followed the current international declaration of Helsinki for human experimentation.

The following examples represent specific embodiments of the disclosure; however, the present disclosure is not limited to these examples.

Example 1

Effect of an Antisense Oligonucleotide in a 7-day Treatment Cycle on Pancreatic Carcinoma A pharmaceutical composition comprising an antisense oligonucleotide of SEQ ID NO. 22 was administered intravenously as a $2^{nd}$, $3^{nd}$ and or $4^{th}$ line treatment to a patient suffering from an advanced pancreatic carcinoma, i.e., the patients had been pretreated with one, two or three other tumor therapies. A portable pump was used to infuse the pharmaceutical composition and the antisense oligonucleotide of SEQ ID No. 22, respectively, intravenously at an infusion speed of 0.8 mL/h via a pre-implanted port access system. Alternatively, the pharmaceutical composition and the antisense oligonucleotide of SEQ ID No. 22, respectively, were administered intravenously with a syringe.

The pharmaceutical composition comprising the antisense oligonucleotide of SEQ ID NO. 22 is administered intravenously in 1 to 10 treatment cycles, wherein one cycle consists of 7 days, followed by a 7-day treatment free interval.

17 patients were treated with this treatment schedule, i.e., receiving a 7-day continuous intravenous infusion of the pharmaceutical composition comprising the antisense oligonucleotide of SEQ ID No. 22, followed by a 7-day interval free of treatment. These patients were enrolled in four successive cohorts with increasing doses:

Cohort 1: 4 patients received 40 mg/m$^2$/d
Cohort 2: 3 patients received 80 mg/m$^2$/d
Cohort 3: 6 patients received 160 mg/m$^2$/d
Cohort 4: 4 patients received 240 mg/m$^2$/d.

The results in Table 1 show that a dose of 80 mg/m$^2$/d in a 7-day treatment cycle, i.e., a total amount of 560 mg/m$^2$/cycle of antisense oligonucleotide unexpectedly has the best effect in the prolongation of the survival rate of the patients, which is 13.8 months. In contrast, doses of 160 mg/m$^2$/d or 240 mg/m$^2$/d show a lower effect compareable with the effect of 40 mg/m$^2$/d.

TABLE 1

| | 7-day continuous infusion, every 2 weeks | | | |
|---|---|---|---|---|
| | 40 mg/m$^2$/d | 80 mg/m$^2$/d | 160 mg/m$^2$/d | 240 mg/m$^2$/d |
| N | 4 | 3 | 6 | 4 |
| Number of events (death) | 4 (100.0%) | 2 (66.7%) | 6 (100.0%) | 4 (100.0%) |
| Median [days] (95% CI) | 209 (33.0-337.0) | 421 (139.0-*) | 86 (65.0-120.0) | 198 (56.0-280.0) |
| Median [weeks] | 29.9 | 60.1 | 12.3 | 28.2 |
| Median [months] | 6.9 | 13.8 | 2.8 | 6.5 |

*An upper limit of 95% CI for 80 mg/m$^2$/d cannot be indicated at the moment as one patient is still alive.

Example 2

Effect of an Antisense Oligonucleotide in a 4-day Treatment Cycle on Pancreatic Carcinoma In another experiment, the pharmaceutical composition comprising the antisense oligonucleotide of SEQ ID NO. 22 is administered intravenously in 1 to 10 cycles, wherein one treatment cycle consists of 4 days, followed by a 10-day treatment free interval.

16 patients were enrolled in four cohorts, which were treated with increased doses of SEQ ID NO. 22:
Cohort A1: 5 patients received 140 mg/m$^2$/d
Cohort A2: 3 patients received 190 mg/m$^2$/d
Cohort A3: 5 patients received 250 mg/m$^2$/d
Cohort A4: 3 patients received 330 mg/m$^2$/d.

Patient 1 of cohort A1 was a 65 years old man, who died 5.5 months after start of treatment, patient 2 was a 50 years old woman, who died 15.6 months after start of treatment, patient 3 was a 44 years old man, who died 4.9 months after start of treatment, and patient 5 was a 63 years old woman, who died 13.4 after start of treatment. Patient 4 of cohort A1 is still alive 14.8 months after start of treatment.

The results of cohort A2 present a lower Median Overall Survival between 5.5 and 9.3 months. Patient 1, a 53 years old woman died 3 months after start of treatment and patient 2, a 63 years old man died 9.2 months after start of treatment; patient 3 is still alive 5.5 months after treatment.

The results of the different cohorts are presented in Table 2, which show high efficiency regarding the survival rate at a dose of 140 mg/m$^2$/d in a 4-day treatment cycle, i.e., a total amount of 560 mg/m$^2$/cycle of the antisense oligonucleotide of SEQ ID NO. 22. This dose leads to an unexpected prolongation of the survival rate, which is 13.4 months. The dose of 140 mg/m$^2$/d in the 4-day treatment cycle led to an prolongation of the survival rate which is comparable with the survival rate of the 80 mg/m$^2$/d in the 7-day treatment cycle.

TABLE 2

| | 4-day continuous infusion, followed by 10-day treatment free interval | | | |
|---|---|---|---|---|
| | 140 mg/m$^2$/d | 190 mg/m$^2$/d | 250 mg/m$^2$/d | 330 mg/m$^2$/d |
| N | 5 | 3 | 5 | 3 |
| Number of events (death) | 3 (60.0%) | 2 (66.7%) | 0 (0.0%) | 0 (0.0%) |
| Median [days] (95% CI) | 476 (150.0-476.0) | (91.0-*) | (—) | (—) |
| Median [weeks] | 58.4 | | | |
| Median [months] | 13.4 | 5.5-9.3 | ** | *** |

*An upper limit of 95% CI for 190 mg/m$^2$/d cannot be indicated at the moment as one patient is still alive.
** The Median Overall Survival of 250 mg/m$^2$/d, and
*** the Median Overall Survival of 330 mg/m$^2$/d cannot be indicated at the moment as all patients are still alive.

Example 3

Successful Use of an Antisense Oligonucleotide for the Preparation of a Pharmaceutical Composition for the Treatment of a Pancreatic Carcinoma A 54-year old male patient with a medical history including diabetes mellitus, arterial hypertension, lymphatic edema, teratoma of the left testis, was diagnosed with pancreatic cancer AJCC (American Joint Committee on Cancer) stage 1. Histology showed a ductal Grade 2 adenocarcinoma. The patient immediately underwent a surgical resection of the tumor (Whipple's procedure, resection grade R0) and received three chemotherapy regimens (containing 5-fluorouracil, leucovorin, and gemcitabine).

After tumor recurrence with metastatic liver metastases based on metastatic pancreatic carcinoma, the patient was treated with a pharmaceutical composition comprising the antisense oligonucleotide of SEQ ID 22 in a dose of 80 mg/m$^2$/d over 7 days representing one cycle of treatment. The patient underwent 7 cycles of a 7-day treatment period, wherein all the cycles were followed by a 7-day treatment free interval.

The identified liver metastases shrunk within 8 weeks from the start of the treatment and completely disappeared within 16 weeks from the beginning of the treatment. Until August 2008, 38.1 months after start of treatment with a pharmaceutical composition comprising the antisense oligonucleotide of SEQ ID No. 22, neither recurrence of primary tumor nor any new metastasis was observed on the abdominal CTs performed in periodic intervals. The patient did not receive any anti-tumor therapy after completion of the treatment with the pharmaceutical composition comprising the antisense oligonucleotide of SEQ ID No. 22. The last control CT available confirmed the complete response.

Example 4

Median Survival in Pancreatic Carcinoma, Malignant Melanoma and Colorectal Carcinoma 11 patients suffering from advanced pancreatic carcinoma, 2 from advanced malignant melanoma, and 4 from advanced colorectal carcinoma were treated with a pharmaceutical composition comprising the antisense oligonucleotide of SEQ ID No. 22 in a dose of either 80 mg/m$^2$/d for 7 days (one cycle) followed by a 7-days treatment free interval or in a dose of 140 mg/m$^2$/d for 4 days (one cycle), followed by a 10-days treatment free interval. The patients were treated for 1 to 10 cycles.

Table 3 shows the median survival in weeks and months, leading to the result that the antisense oligonucleotide of SEQ ID No. 22 in a dose of 80 mg/m$^2$/d clearly prolonged the survival of the patients independent of the type of cancer.

TABLE 3

| | Pancreatic Carcinoma (Stage IVa/IVb) | Malignat Melanoma (Stage III/IV) | Colorectal Carcinoma (Stage III/IV) |
|---|---|---|---|
| Number of Patients | 11 | 2 | 4 |
| Median Survival in weeks [months] | 29.6 (6.8) | 33.9 (7.8) | 17.9 (4.1) |

Example 5

Dose Dependency of $C_{max}$ in Plasma

The dose dependency was measured with a validated capillary gel electrophoresis method. Plasma samples of the patients mentioned in Example 1 (Cohort A1 to A4) and Example 2 (Cohort A1 to A4) were investigated regarding the concentration of the antisense oligonucleotide of SEQ ID No. 22 (FIGS. 3 and 4), wherein the antisense oligonucleotide was administered in the above mentioned doses for 7 or 4 days. The administration of the antisense oligonucleotide of SEQ ID NO. 22 in a dose of 80 mg/m$^2$/d for 7 days (FIG. 3) or in a dose of 140 mg/m$^2$/d for 4 days (FIG. 4), lead both to a total amount of 560 mg/m$^2$/d of the administered antisense oligonucleotide. However, the administration of the antisense oligonucleotide for 4 days (FIG. 4) surprisingly leads to a higher $C_{max}$ than the administration for 7 days (FIG. 3).

Example 6

Dose Dependency of AUC$_{0-t\,last}$ in Plasma

The dose dependency was measured with a validated capillary gel electrophoresis method and subsequent pharmakokinetic analysis with the validated WinNonlin pharmakokinetic software (version 3.2, Pharsight Corp., Mountain View, Calif., USA). The plasma samples of the patients of Example 1 and 2 were further investigated regarding the AUC$_{0-t\,last}$ of the different doses of the antisense oligonucleotide of SEQ ID NO. 22 administered for 7 or 4 days (FIGS. 5 and 6). The results show that even if the administration of 80 mg/m$^2$/d for 7 days and of 140 mg/m$^2$/d for 4 days lead to a total amount of 560 mg/m$^2$/d of the antisense oligonucleotide, the administration of 4 days unexpectedly results in a higher AUC, i.e., a higher bioavailability of the antisense oligonucleotide in the plasma (FIG. 5) than the administration for 7 days (FIG. 6).

---

What is claimed is:

1. A method for treating pancreatic carcinoma or malignant melanoma consisting of: intravenously administering only an antisense oligonucleotide of sequence SEQ ID NO: 22 in an amount of between about 400 to about 800 mg/m$^2$/treatment cycle, wherein a treatment cycle consists of an administration cycle that is the time taken for a first administration of about 400 to about 800 mg/m$^2$ of the oligonucleotide, and, if any further administration cycle is performed, the time interval between consecutive administration cycles.

2. The method according to claim 1, wherein the antisense oligonucleotide is intravenously administered in an amount of between about 560 to about 760 mg/m$^2$/treatment cycle.

3. The method according to claim 1, wherein the antisense oligonucleotide is administered in at least one cycle selected from the group consisting of: 1, 2, 3, 4, 5, 6, 7, 8, 9, 10, 11, 12, 13, 14, and 15 cycles.

4. The method according to claim 3, wherein the antisense oligonucleotide is administered in at least one cycle selected from the group consisting of: 1d, 2d, 3d, 4d, 5d, 6d, 7d, 8d, 9d, 10d, 11d, 12d, 13d, 14d, and 15d per cycle.

5. The method according to claim 4, wherein the antisense oligonucleotide is administered on consecutive days.

6. The method according to claim 3, wherein the time interval between the cycles is selected from the group consisting of: 1d, 2d, 3d, 4d, 5d, 6d, 7d, 8d, 9d, 10d, 11d, 12d, 13d, 14d, and 15d.

7. The method according to claim 1, wherein the antisense oligonucleotide is administered in 1 to 10 cycles.

8. The method according to claim 1, wherein the treatment cycle comprises the administration of either 80 mg/m$^2$/d for 7 days followed by a 7-day treatment free interval or 140 mg/m$^2$/d or 190 mg/m$^2$/d for 4 days followed by a 10-day treatment free interval.

* * * * *

UNITED STATES PATENT AND TRADEMARK OFFICE
CERTIFICATE OF CORRECTION

| | | |
|---|---|---|
| PATENT NO. | : 8,822,425 B2 | Page 1 of 1 |
| APPLICATION NO. | : 12/453487 | |
| DATED | : September 2, 2014 | |
| INVENTOR(S) | : Karl-Hermann Schlingensiepen et al. | |

It is certified that error appears in the above-identified patent and that said Letters Patent is hereby corrected as shown below:

On the Title Page

Please add item (30) Foreign Application Priority Data "Nov. 14, 2008 (EPO).............08 169 181.8"

Signed and Sealed this
Twenty-third Day of December, 2014

Michelle K. Lee
*Deputy Director of the United States Patent and Trademark Office*